US010017550B2

(12) United States Patent
Niederweis et al.

(10) Patent No.: US 10,017,550 B2
(45) Date of Patent: Jul. 10, 2018

(54) ***MYCOBACTERIUM TUBERCULOSIS* PORINS AND TOXINS AND RELATED METHODS**

(75) Inventors: Michael Niederweis, Homewood, AL (US); Olga Danilchanka, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/342,057

(22) PCT Filed: Aug. 30, 2012

(86) PCT No.: PCT/US2012/053091
§ 371 (c)(1),
(2), (4) Date: May 30, 2014

(87) PCT Pub. No.: WO2013/033363
PCT Pub. Date: Mar. 7, 2013

(65) Prior Publication Data

US 2014/0302095 A1 Oct. 9, 2014

Related U.S. Application Data

(60) Provisional application No. 61/529,010, filed on Aug. 30, 2011.

(51) Int. Cl.

| | |
|---|---|
| ***C07K 14/35*** | (2006.01) |
| ***G01N 33/68*** | (2006.01) |
| ***G01N 27/327*** | (2006.01) |
| ***G01N 33/50*** | (2006.01) |
| ***A61K 39/00*** | (2006.01) |

(52) U.S. Cl.
CPC ........... *C07K 14/35* (2013.01); *G01N 27/327* (2013.01); *G01N 33/5008* (2013.01); *G01N 33/6872* (2013.01); *A61K 39/00* (2013.01); *C07K 2319/21* (2013.01); *C07K 2319/22* (2013.01); *C07K 2319/40* (2013.01); *C07K 2319/42* (2013.01); *C07K 2319/50* (2013.01); *G01N 2333/35* (2013.01)

(58) Field of Classification Search
None
See application file for complete search history.

(56) References Cited

U.S. PATENT DOCUMENTS 7,393,540 B2 7/2008 James et al.
2010/0150966 A1 6/2010 Oesch et al.

FOREIGN PATENT DOCUMENTS

WO WO 03/004520 * 1/2003
WO WO 2003/0045420 * 1/2003
WO 2006110728 10/2006
WO WO 2008/135067 * 11/2008
WO 2010034018 3/2010
WO 2013033363 3/2013

OTHER PUBLICATIONS

Alahari et al. Journal of Bacteriology, Sep. 2007, p. 6351-6358 vol. 189, No. 17.*
Gibbons et al. Journal of Bacteriology, vol. 189, No. 14, Jul. 2007, p. 5090-5100.*
Danilchanka et al. Presentation Abstract. MtpA, a Novel Porin of *Mycobacterium tuberculosis*. 110th General Meeting of the American Society of Microbiology May 23, 2010.*
UniprotKB-O05442 (CPNT_MYCTU) , Jul. 1997.*
Agu et al., Bacteriophage-encoded toxins: the lambda-holin protein causes caspase-independent non-apoptotic cell death of eukaryotic cells. Cell Microbiol 9:1753-65.
Alahari et al., The N-Terminal Domain of OmpATb is Required for Membrane Translocation and Pore-Forming Activity in Mycobacteria, Journal of Bacteriology, vol. 189, No. 17, Sep. 2007, pp. 6351-6358.
Andreu, et al., Cell population heterogeneity in *Mycobacterium tuberculosis* H37Rv. Tuberculosis (Edinb), 88 (2008), pp. 553-559.
Barry, Interpreting cell wall 'virulence factors' of *Mycobacterium tuberculosis*, Trends Microbiol. vol. 9, 2001, pp. 237-241.
Bendtsen et al., Improved prediction of signal peptides: SignalP 3.0., J. Mol. Biol. vol. 340, Jul. 16, 2004, pp. 783-795.
Bensalah et al., New circulating biomarkers for prostate cancer, Prostate Cancer and Prostatic Diseases, vol. 11, 2008, pp. 112-120.
Benz et al., Formation of large, ion-permeable membrane channels by the matrix protein (porin) of *Escherichia coli*, Biochim. Biophys. Acta. , vol. 511, 1978, pp. 305-319.
Brennan, Structure, function, and biogenesis of the cell wall of *Mycobacterium tuberculosis*, Tuberculosis (Edinb), vol. 83, 2003, pp. 91-97.
Brennan et al., The envelope of mycobacteria, Annu. Rev. Biochem., vol. 64, 1995, pp. 29-63.
Briones et al. Cre reporter system to monitor the translocation of type III secreted proteins into host cells. Infect Immun 74 (2006), pp. 1084-1090.
Carinato et al., The apeE gene of *Salmonella typhimurium* encodes an outer membrane esterase not present in *Escherichia coli*. J Bacteriol 180 (1998), pp. 3517-3521.
Cascioferro et al., PE is a functional domain responsible for protein translocation and localization on mycobacterial cell wall, Mol. Microbiol., vol. 66, 2007, pp. 1536-1547.

(Continued)

*Primary Examiner* — Oluwatosin A Ogunbiyi
(74) *Attorney, Agent, or Firm* — Kilpatrick Townsend & Stockton LLP

(57) ABSTRACT

Provided herein are isolated polypeptides comprising the amino-terminal domain of *Mycobacterium tuberculosis* porin A (MtpA), wherein the polypeptide is a porin monomer. Also provided are isolated polypeptides comprising the carboxy-terminal domain of *Mycobacterium tuberculosis* porin A, wherein the polypeptide is a toxin. Also provided are methods of treating or preventing a *Mycobacterium tuberculosis* (Mtb) infection in a subject with or at risk of developing a Mtb infection. Further provided are chimeric porin polypeptides comprising a first polypeptide comprising an amino-terminal domain of *Mycobacterium tuberculosis* porin and a second polypeptide comprising an antigen and the use the chimeric porin polypeptides in methods of eliciting an immune response in a subject.

5 Claims, 9 Drawing Sheets

(56) References Cited

OTHER PUBLICATIONS

Cover et al., Helicobacter pylori VacA, a paradigm for toxin multifunctionality, Nat Rev Microbiol., vol. 3, 2005, pp. 320-332.
Danilchanka et al., Identification of novel multidrug efflux pump of *Mycobacterium tuberculosis*, Antimicrobial Agents and Chemotherapy. vol. 52, No. 7, May 5, 2008, pp. 2503-2511.
Danilchanka et al, MtPA, a Novel Porin of *Mycobacterium tuberculosis*, American Society of Microbiology Meeting, San Diego, May 26, 2010.
Danilchanka et al., Role of porins for uptake of antibiotics by *Mycobacterium smegmatis*, Antimicrob Agents Chemother., vol. 52, 2008b, pp. 3127-3134.
Danilchanka, "Diffusion pathways through the outer membrane of Mycobacteria", Ph .D. Thesis , University of Alabama at Birmingham, 2009, pp. 59 and 79-116.
Danke et al., Adjusting transgene expression levels in lymphocytes with a set of inducible promoters. J Gene Med 12 (2010), pp. 501-515.
Davis et al., The role of the granuloma in expansion and dissemination of early tuberculous infection. Cell 136 (2009), pp. 37-49.
De Keyzer et al., The bacterial translocase: a dynamic protein channel complex, Cell Mol. Life Sci., vol. 60, No. 10, Oct. 2003, pp. 2034-2052.
Desvaux et al., The unusual extended signal peptide region of the type V secretion system is phylogenetically restricted, FEMS Microbiol. Lett. vol. 264, Issue. 1, Nov. 2006, pp. 22-30.
Disis et al., Breast Disease, vol. 20, 2004, pp. 3-11.
Fabrino et al., Porins facilitate nitric oxide-mediated killing of mycobacteria, Microbes Infect., vol. 11, 2009, pp. 868-875.
Fernandez-Patron et al., Reverse staining of sodium dodecyl sulfate polyacrylamide gels by imidazole-zinc salts: sensitive detection of unmodified proteins, Biotechniques, vol. 12, No. 4, Apr. 1992, pp. 564-573.
Flores et al., Genetic analysis of the beta-lactamases of *Mycobacterium tuberculosis* and *Mycobacterium smegmatis* and susceptibility to beta-lactam antibiotics. Microbiology 151 (2005), pp. 521-532.
Franzblau et al., Rapid, low-technology MIC determination with clinical *Mycobacterium tuberculosis* isolates by using the microplate Alamar Blue assay, J. Clin. Microbiol., vol. 36 issue 2, Feb. 1998, pp. 362-366.
Garcia et al., Measurement of effector protein injection by type III and type IV secretion systems by using a 13-residue phosphorylatable glycogen synthase kinase tag. Infect Immun 74 (2006), pp. 5645-5657.
Graycar et al., Human transforming growth factor-beta 3: recombinant expression, purification, and biological activities in comparison with transforming growth factors-beta 1 and -beta 2, Mol. Endocrinol., vol. 3, 1977-1986.
Hagedorn et al., Infection by tubercular mycobacteria is spread by nonlytic ejection from their amoeba hosts. Science 323 (2009), pp. 1729-1733.
Henderson et al., Type V protein secretion pathway: the autotransporter story. Microbiol Mol Biol Rev 68 (2004), pp. 692-744.
Hoffmann et al., Disclosure of the mycobacterial outer membrane: Cryo-electron tomography and vitreous sections reveal the lipid bilayer structure, Proc. Natl. Acad. Sci. USA, vol. 105, 2008, pp. 3963-3967.
Hoogenboom et al., "By-passing immunization: Human antibodies from synthetic repertoires of germline VH gene segments rearranged in vitro"; Journal of Molecular Biology, vol. 227, No. 2, pp. 381-388, Sep. 1992.
Huff et al., Taking phage integration to the next level as a genetic tool for mycobacteria. Gene 468 (2010), pp. 8-19.
Jacob-Dubuisson et al., Two-partner secretion in Gram-negative bacteria: a thrifty, specific pathway for large virulence proteins, Mol. Microbiol., vol. 40, No. 2, Apr. 2001, pp. 306-313.
Jaeger et al., Improved predictions of secondary structures for RNA, Proc. Natl. Acad. Sci. USA, vol. 86, Oct. 1989, pp. 7706-7710.
Jager et al., Clinical cancer vaccine trials, Curr. Opin. Immunol., vol. 14, No. 2, Apr. 2002, pp. 178-182.
Jaeger et al., Predicting optimal and suboptimal secondary structure for RNA, Methods in Enzymology, vol. 183, 1989, pp. 281-306.
Jakobovits et al., "Germ-line transmission and expression of a human-derived yeast artificial chromosome", Nature, vol. 362, No. 6417, pp. 255-258, Mar. 1993.
Jordao et al., On the killing of mycobacteria by macrophages, Cell Microbiology, vol. 10, Issue 2, 2008, pp. 529-548.
Kaps et al., Energy transfer between fluorescent proteins using a co-expression system in Mycobacteriumsmegmatis, Gene, vol. 278, Issue 1-2, Oct. 31, 2001, pp. 115-124.
Kartmann et al., Porins in the cell wall of *Mycobacterium tuberculosis*, J. Bacteriol., vol. 181; Issue 24, Dec. 1999, p. 7650.
Lee et al., The pore size of the autotransporter domain is critical for the active translocation of the passenger domain. Biochem Biophys Res Commun 307 (2003), pp. 820-825.
Lichtinger et al., Evidence for a small anionselective channel in the cell wall *Mycobacterium bovis* BCG besides a wide cation-selective pore, FEBS Lett., vol. 454, 1999, pp. 349-355.
Liu et al., Regulation of porin-mediated outer membrane permeability by nutrient limitation in *Escherichia coli*, J. Bacteriol. vol. 180, 1998, pp. 3917-3922.
McCann et al., Beta-lactamase can function as a reporter of bacterial protein export during *Mycobacterium tuberculosis* infection of host cells. Microbiology 153 (2007), pp. 3350-3359.
McNeel, Cancer Chemother. Biol. Response Modif, vol. 22. 2005, pp. 247-261.
Macmicking et al., Nitric oxide and macrophage function, Annu. Rev. Immunol., vol. 15, 1997, pp. 323-350.
Mailaender et al., The MspA porin promotes growth and increases antibiotic susceptibility of both *Mycobacterium bovis* BCG and *Mycobacterium tuberculosis*, Microbiology, vol. 150, 2004, pp. 853-864.
Molloy et al., Proteomic analysis of the *Escherichia coli* outer membrane, Eur. J. Biochem., vol. 267, 2000, pp. 2871-2881.
Muhlradt et al., Asymmetrical distribution and artifactual reorientation of lipopolysaccharide in the outer membrane bilayer of *Salmonella typhimurium*, Eur. J. Biochem., vol. 51, 1975, pp. 343-352.
Niederweis et al., Mycobacterial outer membranes: in search of proteins, Trends Microbiol., vol. 18, 2010, pp. 109-116.
Niederweis, Mycobacterial porins—new channel proteins in unique outer membranes, Mol. Microbiol., vol. 49, 2003, pp. 1167-1177.
Niederweis, Nutrient acquisition by mycobacteria, Microbiology, vol. 154, 2008, pp. 679-692.
Nikaido, Molecular basis of bacterial outer membrane permeability revisited, Microbiol. Mol. Biol. Rev., vol. 67, 2003, pp. 593-656.
Obata et al., Identification of cancer antigens in breast cancer by the SEREX expression cloning method, Breast Cancer, vol. 6, Oct. 1999, pp. 305-311.
Oh et al., "siRNA delivery systems for cancer treatment", Advanced Drug Delivery Reviews, vol. 61, No. 10.
Pages et al., The porin and the permeating antibiotic: a selective diffusion barrier in Gram-negative bacteria, Nat. Rev. Microbiol., vol. 6, 2008, pp. 893-903.
Pandey et al., Nitrile-inducible gene expression in mycobacteria, Tuberculosis (Edinb), vol. 89, 2009, pp. 12-16.
International Application No. PCT/US2012/053091, International Search Report and Written Opinion dated Dec. 14, 2013, 16 pages.
Purdy et al., Decreased outer membrane permeability protects mycobacteria from killing by ubiquitin-derived peptides, Mol. Microbiol., vol. 73, Issue 5, Sep. 2009, pp. 844-857.
Ray et al., Life on the inside: the intracellular lifestyle of cytosolic bacteria. Nat Rev Micobiol 7 (2009), pp. 333-340.
Raynaud et al., The functions of OmpATb, a pore-forming protein of *Mycobacterium tuberculosis*, Molecular Microbiology (2002) 46(1), pp. 191-201.
Saleh et al., Melanoma Immunotherapy: Past, Present, and Future, Current Pharmaceutical Design, vol. 11, 2005, pp. 3461-3473.

(56) References Cited

OTHER PUBLICATIONS

Sambandamurthy et al., Live attenuated mutants of *Mycobacterium tuberculosis* as candidate vaccines against tuberculosis, Microbes Infect. vol. 7, Issue 5-6, May 2005, pp. 955-961.
Schulz, Porins: general to specific, native to engineered passive pores, Curr. Opin. Struct. Biol., vol. 6, Issue 4, Aug. 1996, pp. 485-490.
Senaratne et al., Expression of a Gene for a Porin-Like Protein of the OmpA Family from *Mycobacterium tuberculosis* H37Rv, Journal of Bacteriology, Jul. 1998, vol. 180, No. 14, pp. 3541-3547.
Siroy et al., Rv1698 of *Mycobacterium tuberculosis* represents a new class of channel-forming outer membrane proteins, J. Biol. Chem., vol. 283, 2008, pp. 17827-17837.
Smeulders et al., Adaptation of *Mycobacterium smegmatis* to Stationary Phase, Journal of Bacteriology, vol. 181, No. 1, Jan. 1999, pp. 270-283.
Song et al., Identification of outer membrane proteins of *Mycobacterium tuberculosis*, Tuberculosis, vol. 88, 2008, pp. 526-544.
Song et al. "Expression of the ompATb operon accelerates ammonia secretion and adaptation of *Mycobacterium tuberculosis* to acidic environments," vol. 80, 2011, pp. 900-918.
Sonpavde et al., Vaccine therapy for prostate cancer, Urol. Oncol., vol. 25, Issue 6, Nov. 2007, pp. 451-459.
Stahl et al., MspA provides the main hydrophilic pathway through the cell wall of *Mycobacterium smegmatis*, Mol. Microbiol. vol. 40, Issue 2, Apr. 2001, pp. 451-464.
Stephan et al., Multidrug Resistance of a Porin Deletion Mutant of *Mycobacterium smegmatis*, Antimicrob. Agents Chemother., vol. 48, Issue 11, 2004, pp. 4163-4170.
Stephan et al., The growth rate of *Mycobacterium smegmatis* depends on sufficient porinmediated influx of nutrients, Mol. Microbiol., vol. 58, 2005, pp. 714-730.
Suri, Cancer testis antigens—their importance in immunotherapy and in the early detection of cancer, Expert Opin. Biol. Ther., vol. 6, Issue 4, Apr. 2006, pp. 379-389.
Szabady et al., An unusual signal peptide facilitates late steps in the biogenesis of bacterial autotransporter, Proc. Natl. Acad. Sci. USA, vol. 102, Issue 1, 2005, pp. 221-226.
Vandal et al., A membrane protein preserves intrabacterial pH in intraphagosomal *Mycobacterium tuberculosis*. Nat Med 14 (2008), pp. 849-854.
Wang et al., Phase variation in Xenorhabdus luminescens: cloning and sequencing of the lipase gene and analysis of its expression in primary and secondary phases the of bacterium. J Bacteriol 175 (1993), pp. 1665-1673.
Wilhelm et al., A novel lipolytic enzyme located in the outer membrane of *Pseudomonas aeruginosa*. J Bacteriol 181 (1999), pp. 6977-6986.
Wolfe et al., Proteomic Definition of Cell Wall of *Mycobacterium tuberculosis*, Journal of Proteom Research, vol. 9, Sep. 2010, pp. 5816-5826.
Wolschendorf et al., Porins Are Required for Uptake of Phosphates by *Mycobacterium smegmatis*, J. Bacteriol. vol. 189, Issue 6, Jan. 2007, pp. 2435-2442.uri.
Zhang et al., Recombinant *Mycobacterium smegmatis* Expressing an ESAT6-CFP10 Fusion Protein Induces Anti-Mycobacterial Immune Responses and Protects Against *Mycobacterium tuberculosis* Challenge in Mice, Scand. J. Immunol., vol. 72, Issue 4, Oct. 2010, pp. 349-357.
Zimmerman et al., Function of the outer membrane of *Escherichia coli* as a permeability barrier to beta-lactam antibiotics. Antimicrob. Agents Chemother. 12 (1997), pp. 368-372.
Zuber et al., Direct visualization of the outer membrane of mycobacteria and corynebacteria in their native state, J Bacteriol., vol. 190, 2008, pp. 5672-5680.
Zuker, On finding all suboptimal foldings of an RNA molecule, Science, vol. 244. No. 4900, Apr. 7, 1989, pp. 48-52.
Japanese Patent Application No. JP2014-528593, Office Action, dated Jul. 1, 2016, 15 pages (6 pages for JP OA, 9 pages English Translation).
Office action in related European Patent Application No. 12 827 230.9, dated Jan. 17, 2017, 5 pages.
Danilchanka et al. "MtpA, a Novel Porin of *Mycobacterium tuberculosis*," Poster Presentation at the 110th General Meeting of the American Society of Microbiology (2010).

* cited by examiner

SEQUENCE LISTING

<160> NUMBER OF SEQ ID NOS: 15

<210> SEQ ID NO 1
<211> LENGTH: 846
<212> TYPE: PRT
<213> ORGANISM: Mycobacterium tuberculosis

<400> SEQUENCE: 1

```
Met Ala Pro Leu Ala Val Asp Pro Ala Ala Leu Asp Ser Ala Gly Gly
1               5                   10                  15

Ala Val Val Ala Ala Gly Ala Gly Leu Gly Ala Val Ile Ser Ser Leu
            20                  25                  30

Thr Ala Ala Leu Ala Gly Cys Ala Gly Met Ala Gly Asp Asp Pro Ala
        35                  40                  45

Gly Ala Val Phe Gly Arg Ser Tyr Asp Gly Ser Ala Ala Ala Leu Val
    50                  55                  60

Gln Ala Met Ser Val Ala Arg Asn Gly Leu Cys Asn Leu Gly Asp Gly
65                  70                  75                  80

Val Arg Met Ser Ala His Asn Tyr Ser Leu Ala Glu Ala Met Ser Asp
                85                  90                  95

Val Ala Gly Arg Ala Ala Pro Leu Pro Ala Pro Pro Pro Ser Gly Cys
            100                 105                 110

Val Gly Val Gly Ala Pro Pro Ser Ala Val Gly Gly Gly Gly Gly Ala
        115                 120                 125

Pro Lys Gly Trp Gly Trp Val Ala Pro Tyr Ile Gly Met Ile Trp Pro
    130                 135                 140

Asn Gly Asp Ser Thr Lys Leu Arg Ala Ala Ala Val Ala Trp Arg Ser
145                 150                 155                 160

Ala Gly Thr Gln Phe Ala Leu Thr Glu Ile Gln Ser Thr Ala Gly Pro
                165                 170                 175

Met Gly Val Ile Arg Ala Gln Gln Leu Pro Glu Ala Gly Leu Ile Glu
            180                 185                 190

Ser Ala Phe Ala Asp Ala Tyr Ala Ser Thr Thr Ala Val Val Gly Gln
        195                 200                 205

Cys His Gln Leu Ala Ala Gln Leu Asp Ala Tyr Ala Ala Arg Ile Asp
    210                 215                 220

Ala Val His Ala Ala Val Leu Asp Leu Leu Ala Arg Ile Cys Asp Pro
225                 230                 235                 240

Leu Thr Gly Ile Lys Glu Val Trp Glu Phe Leu Thr Asp Gln Asp Glu
                245                 250                 255

Asp Glu Ile Gln Arg Ile Ala His Asp Ile Ala Val Val Val Asp Gln
            260                 265                 270

Phe Ser Gly Glu Val Asp Ala Leu Ala Ala Glu Ile Thr Ala Val Val
        275                 280                 285

Ser His Ala Glu Ala Val Ile Thr Ala Met Ala Asp His Ala Gly Lys
    290                 295                 300

Gln Trp Asp Arg Phe Leu His Ser Asn Pro Val Gly Val Val Ile Asp
```

-continued

```
305                 310                 315                 320

Gly Thr Gly Gln Gln Leu Lys Gly Phe Gly Glu Glu Ala Phe Gly Met
                325                 330                 335

Ala Lys Asp Ser Trp Asp Leu Gly Pro Leu Arg Ala Ser Ile Asp Pro
            340                 345                 350

Phe Gly Trp Tyr Arg Ser Trp Glu Glu Met Leu Thr Gly Met Ala Pro
        355                 360                 365

Leu Ala Gly Leu Gly Gly Glu Asn Ala Pro Gly Val Val Glu Ser Trp
    370                 375                 380

Lys Gln Phe Gly Lys Ser Leu Ile His Trp Asp Glu Trp Thr Thr Asn
385                 390                 395                 400

Pro Asn Glu Ala Leu Gly Lys Thr Val Phe Asp Ala Ala Thr Leu Ala
                405                 410                 415

Leu Pro Gly Gly Pro Leu Ser Lys Leu Gly Ser Lys Gly Arg Asp Ile
            420                 425                 430

Leu Ala Gly Val Arg Gly Leu Lys Glu Arg Leu Glu Pro Thr Thr Pro
        435                 440                 445

His Leu Glu Pro Pro Ala Thr Pro Pro Arg Pro Gly Pro Gln Pro Pro
    450                 455                 460

Arg Ile Glu Pro Pro Glu Ser Gly His Pro Ala Pro Ala Pro Ala Ala
465                 470                 475                 480

Lys Pro Ala Pro Val Pro Ala Asn Gly Pro Leu Pro His Ser Pro Thr
                485                 490                 495

Glu Ser Lys Pro Pro Pro Val Asp Arg Pro Ala Glu Pro Val Ala Pro
            500                 505                 510

Ser Ser Ala Ser Ala Gly Gln Pro Arg Val Ser Ala Ala Thr Thr Pro
        515                 520                 525

Gly Thr His Val Pro His Gly Leu Pro Gln Pro Gly Glu His Val Pro
    530                 535                 540

Ala Gln Ala Pro Pro Ala Thr Thr Leu Leu Gly Gly Pro Pro Val Glu
545                 550                 555                 560

Ser Ala Pro Ala Thr Ala His Gln Pro Gln Trp Ala Thr Thr Pro Ala
                565                 570                 575

Ala Pro Ala Ala Ala Pro His Ser Thr Pro Gly Gly Val His Ser Thr
            580                 585                 590

Glu Ser Gly Pro His Gly Arg Ser Leu Ser Ala His Gly Ser Glu Pro
        595                 600                 605

Thr His Asp Gly Ala Ser His Gly Ser Gly His Gly Ser Gly Ser Glu
    610                 615                 620

Pro Pro Gly Leu His Ala Pro His Arg Glu Gln Gln Leu Ala Met His
625                 630                 635                 640

Ser Asn Glu Pro Ala Gly Glu Gly Trp His Arg Leu Ser Asp Glu Ala
                645                 650                 655

Val Asp Pro Gln Tyr Gly Glu Pro Leu Ser Arg His Trp Asp Phe Thr
            660                 665                 670

Asp Asn Pro Ala Asp Arg Ser Arg Ile Asn Pro Val Val Ala Gln Leu
        675                 680                 685

Met Glu Asp Pro Asn Ala Pro Phe Gly Arg Asp Pro Gln Gly Gln Pro
    690                 695                 700

Tyr Thr Gln Glu Arg Tyr Gln Glu Arg Phe Asn Ser Val Gly Pro Trp
705                 710                 715                 720

Gly Gln Gln Tyr Ser Asn Phe Pro Pro Asn Asn Gly Ala Val Pro Gly
                725                 730                 735
```

```
Thr Arg Ile Ala Tyr Thr Asn Leu Glu Lys Phe Leu Ser Asp Tyr Gly
            740                 745                 750

Pro Gln Leu Asp Arg Ile Gly Gly Asp Gln Gly Lys Tyr Leu Ala Ile
        755                 760                 765

Met Glu His Gly Arg Pro Ala Ser Trp Glu Gln Arg Ala Leu His Val
    770                 775                 780

Thr Ser Leu Arg Asp Pro Tyr His Ala Tyr Thr Ile Asp Trp Leu Pro
785                 790                 795                 800

Glu Gly Trp Phe Ile Glu Val Ser Glu Val Ala Pro Gly Cys Gly Gln
                805                 810                 815

Pro Gly Gly Ser Ile Gln Val Arg Ile Phe Asp His Gln Asn Glu Met
            820                 825                 830

Arg Lys Val Glu Glu Leu Ile Arg Arg Gly Val Leu Arg Gln
        835                 840                 845


<210> SEQ ID NO 2
<211> LENGTH: 443
<212> TYPE: PRT
<213> ORGANISM: Mycobacterium tuberculosis

<400> SEQUENCE: 2

Met Ala Pro Leu Ala Val Asp Pro Ala Ala Leu Asp Ser Ala Gly Gly
1               5                   10                  15

Ala Val Val Ala Ala Gly Ala Gly Leu Gly Ala Val Ile Ser Ser Leu
            20                  25                  30

Thr Ala Ala Leu Ala Gly Cys Ala Gly Met Ala Gly Asp Asp Pro Ala
        35                  40                  45

Gly Ala Val Phe Gly Arg Ser Tyr Asp Gly Ser Ala Ala Ala Leu Val
    50                  55                  60

Gln Ala Met Ser Val Ala Arg Asn Gly Leu Cys Asn Leu Gly Asp Gly
65                  70                  75                  80

Val Arg Met Ser Ala His Asn Tyr Ser Leu Ala Glu Ala Met Ser Asp
                85                  90                  95

Val Ala Gly Arg Ala Ala Pro Leu Pro Ala Pro Pro Pro Ser Gly Cys
            100                 105                 110

Val Gly Val Gly Ala Pro Pro Ser Ala Val Gly Gly Gly Gly Gly Ala
        115                 120                 125

Pro Lys Gly Trp Gly Trp Val Ala Pro Tyr Ile Gly Met Ile Trp Pro
    130                 135                 140

Asn Gly Asp Ser Thr Lys Leu Arg Ala Ala Ala Val Ala Trp Arg Ser
145                 150                 155                 160

Ala Gly Thr Gln Phe Ala Leu Thr Glu Ile Gln Ser Thr Ala Gly Pro
                165                 170                 175

Met Gly Val Ile Arg Ala Gln Gln Leu Pro Glu Ala Gly Leu Ile Glu
            180                 185                 190

Ser Ala Phe Ala Asp Ala Tyr Ala Ser Thr Thr Ala Val Val Gly Gln
        195                 200                 205

Cys His Gln Leu Ala Ala Gln Leu Asp Ala Tyr Ala Ala Arg Ile Asp
    210                 215                 220

Ala Val His Ala Ala Val Leu Asp Leu Leu Ala Arg Ile Cys Asp Pro
225                 230                 235                 240

Leu Thr Gly Ile Lys Glu Val Trp Glu Phe Leu Thr Asp Gln Asp Glu
                245                 250                 255

Asp Glu Ile Gln Arg Ile Ala His Asp Ile Ala Val Val Val Asp Gln
```

-continued

```
            260                 265                 270

Phe Ser Gly Glu Val Asp Ala Leu Ala Ala Glu Ile Thr Ala Val Val
        275                 280                 285

Ser His Ala Glu Ala Val Ile Thr Ala Met Ala Asp His Ala Gly Lys
    290                 295                 300

Gln Trp Asp Arg Phe Leu His Ser Asn Pro Val Gly Val Val Ile Asp
305                 310                 315                 320

Gly Thr Gly Gln Gln Leu Lys Gly Phe Gly Glu Glu Ala Phe Gly Met
                325                 330                 335

Ala Lys Asp Ser Trp Asp Leu Gly Pro Leu Arg Ala Ser Ile Asp Pro
            340                 345                 350

Phe Gly Trp Tyr Arg Ser Trp Glu Glu Met Leu Thr Gly Met Ala Pro
        355                 360                 365

Leu Ala Gly Leu Gly Gly Glu Asn Ala Pro Gly Val Val Glu Ser Trp
    370                 375                 380

Lys Gln Phe Gly Lys Ser Leu Ile His Trp Asp Glu Trp Thr Thr Asn
385                 390                 395                 400

Pro Asn Glu Ala Leu Gly Lys Thr Val Phe Asp Ala Ala Thr Leu Ala
                405                 410                 415

Leu Pro Gly Gly Pro Leu Ser Lys Leu Gly Ser Lys Gly Arg Asp Ile
            420                 425                 430

Leu Ala Gly Val Arg Gly Leu Lys Glu Arg Leu
        435                 440


<210> SEQ ID NO 3
<211> LENGTH: 196
<212> TYPE: PRT
<213> ORGANISM: Mycobacterium tuberculosis

<400> SEQUENCE: 3

Arg Leu Ser Asp Glu Ala Val Asp Pro Gln Tyr Gly Glu Pro Leu Ser
1               5                   10                  15

Arg His Trp Asp Phe Thr Asp Asn Pro Ala Asp Arg Ser Arg Ile Asn
            20                  25                  30

Pro Val Val Ala Gln Leu Met Glu Asp Pro Asn Ala Pro Phe Gly Arg
        35                  40                  45

Asp Pro Gln Gly Gln Pro Tyr Thr Gln Glu Arg Tyr Gln Glu Arg Phe
    50                  55                  60

Asn Ser Val Gly Pro Trp Gly Gln Gln Tyr Ser Asn Phe Pro Pro Asn
65                  70                  75                  80

Asn Gly Ala Val Pro Gly Thr Arg Ile Ala Tyr Thr Asn Leu Glu Lys
                85                  90                  95

Phe Leu Ser Asp Tyr Gly Pro Gln Leu Asp Arg Ile Gly Gly Asp Gln
            100                 105                 110

Gly Lys Tyr Leu Ala Ile Met Glu His Gly Arg Pro Ala Ser Trp Glu
        115                 120                 125

Gln Arg Ala Leu His Val Thr Ser Leu Arg Asp Pro Tyr His Ala Tyr
    130                 135                 140

Thr Ile Asp Trp Leu Pro Glu Gly Trp Phe Ile Glu Val Ser Glu Val
145                 150                 155                 160

Ala Pro Gly Cys Gly Gln Pro Gly Gly Ser Ile Gln Val Arg Ile Phe
                165                 170                 175

Asp His Gln Asn Glu Met Arg Lys Val Glu Glu Leu Ile Arg Arg Gly
            180                 185                 190
```

-continued

```
Val Leu Arg Gln
        195


<210> SEQ ID NO 4
<211> LENGTH: 15
<212> TYPE: PRT
<213> ORGANISM: Artificial Sequence
<220> FEATURE:
<223> OTHER INFORMATION: linker

<400> SEQUENCE: 4

Gly Gly Gly Gly Ser Gly Gly Gly Gly Ser Gly Gly Gly Gly Ser
1               5                   10                  15


<210> SEQ ID NO 5
<211> LENGTH: 31
<212> TYPE: DNA
<213> ORGANISM: Artificial Sequence
<220> FEATURE:
<223> OTHER INFORMATION: synthetic construct

<400> SEQUENCE: 5

cgcatatggc gccgttggcg gtcgatcccg c                                     31


<210> SEQ ID NO 6
<211> LENGTH: 30
<212> TYPE: DNA
<213> ORGANISM: Artificial Sequence
<220> FEATURE:
<223> OTHER INFORMATION: synthetic construct

<400> SEQUENCE: 6

cgaagcttct actgtcgcaa caccccgcgc                                       30


<210> SEQ ID NO 7
<211> LENGTH: 59
<212> TYPE: DNA
<213> ORGANISM: Artificial Sequence
<220> FEATURE:
<223> OTHER INFORMATION: synthetic construct

<400> SEQUENCE: 7

gcttaattaa cagaaaggag gatttcaact atcatggcgc cgttggcggt cgatcccgc      59


<210> SEQ ID NO 8
<211> LENGTH: 27
<212> TYPE: DNA
<213> ORGANISM: Artificial Sequence
<220> FEATURE:
<223> OTHER INFORMATION: synthetic construct

<400> SEQUENCE: 8

cggatatccg gtgtcgtcgg ctcaagc                                          27


<210> SEQ ID NO 9
<211> LENGTH: 27
<212> TYPE: DNA
<213> ORGANISM: Artificial Sequence
<220> FEATURE:
<223> OTHER INFORMATION: synthetic construct

<400> SEQUENCE: 9

gcttgagccg acgacaccga agcttcg                                          27


<210> SEQ ID NO 10
<211> LENGTH: 32
```

-continued

```
<212> TYPE: DNA
<213> ORGANISM: Artificial Sequence
<220> FEATURE:
<223> OTHER INFORMATION: synthetic construct

<400> SEQUENCE: 10

cgcatatgtg gagccacccg cagttcgaaa aa                                 32


<210> SEQ ID NO 11
<211> LENGTH: 49
<212> TYPE: DNA
<213> ORGANISM: Artificial Sequence
<220> FEATURE:
<223> OTHER INFORMATION: synthetic construct

<400> SEQUENCE: 11

cgaagcttta gtggtggtgg tggtggtgag tactggcgta gtccggcac                49


<210> SEQ ID NO 12
<211> LENGTH: 38
<212> TYPE: DNA
<213> ORGANISM: Artificial Sequence
<220> FEATURE:
<223> OTHER INFORMATION: synthetic construct

<400> SEQUENCE: 12

gccacccgca gttcgaaaaa gcaggtgcag tgtttggc                           38


<210> SEQ ID NO 13
<211> LENGTH: 45
<212> TYPE: DNA
<213> ORGANISM: Artificial Sequence
<220> FEATURE:
<223> OTHER INFORMATION: synthetic construct

<400> SEQUENCE: 13

ggcgtagtcc ggcacgtcgt acgggtacgg cgtggtcggt tccag                    45


<210> SEQ ID NO 14
<211> LENGTH: 58
<212> TYPE: DNA
<213> ORGANISM: Artificial Sequence
<220> FEATURE:
<223> OTHER INFORMATION: synthetic construct

<400> SEQUENCE: 14

agtactggcg tagtccggca cgtcgtacgg gtagatatcc tgtcgcaaca ccccgcgc       58


<210> SEQ ID NO 15
<211> LENGTH: 49
<212> TYPE: DNA
<213> ORGANISM: Artificial Sequence
<220> FEATURE:
<223> OTHER INFORMATION: synthetic construct

<400> SEQUENCE: 15

taaagcttta gtggtggtgg tggtggtgag tactggcgta gtccggcac                49
```

*MYCOBACTERIUM TUBERCULOSIS* PORINS AND TOXINS AND RELATED METHODS

CROSS-REFERENCE TO RELATED APPLICATIONS

This application claims benefit of U.S. Provisional Application No. 61/529,010, filed Aug. 30, 2011, which is hereby incorporated herein by reference in its entirety.

STATEMENT REGARDING FEDERALLY FUNDED RESEARCH

This invention was made with government funding under Grant No. RO1 AI63432 from the National Institutes of Health. The government has certain rights in this invention.

BACKGROUND

*Mycobacterium tuberculosis* (Mtb) has infected about two billion people and the lung of a single infected patient contains more than a billion bacilli. Poor treatment compliance leads to selection and increasing spread of multi- and extremely-drug resistant strains.

SUMMARY

Provided are isolated polypeptides comprising the amino-terminal domain of *Mycobacterium tuberculosis* porin A (MtpA), wherein the polypeptide is a porin monomer. Also provided are isolated polypeptides comprising the carboxy-terminal domain of MtpA, wherein the polypeptide is a toxin.

Also provided are methods of treating or preventing a *Mycobacterium tuberculosis* (Mtb) infection in a subject with or at risk of developing a Mtb infection. The methods comprise administering to the subject a first agent that modulates the activity of a *Mycobacterium tuberculosis* porin (Mtp) and a second agent that treats or prevents the Mtb infection.

Provided herein are chimeric porin polypeptides. The chimeric porin polypeptides comprise a first polypeptide comprising an amino-terminal domain of a *Mycobacterium tuberculosis* porin and a second polypeptide comprising an antigen.

Also provided are methods of eliciting in a subject an immune response to an antigen. The methods comprise administering to the subject a modified *Mycobacterium*, wherein the modified *Mycobacterium* comprises a chimeric porin polypeptide described herein.

*Mycobacterium tuberculosis* porin (Mtp) oligomers are provided herein. The Mtp oligomers can comprise 2 to 12 isolated polypeptides comprising the amino-terminal domain of MtpA.

Also provided are nucleic acid sequences encoding a single-chain *Mycobacterium tuberculosis* porin (Mtp) oligomer. The nucleic acid sequences can comprise at least a first and a second porin encoding nucleotide sequence and a linker nucleic acid sequence encoding an amino acid linker. The first nucleotide sequence can encode a first Mtp monomer and the second nucleotide sequence can encode a second porin monomer.

Methods of detecting an analyte in a conductive liquid medium are provided. The methods comprise applying an electric field to the Mtp oligomers described herein, wherein the Mtp oligomers have a vestibule and a constriction zone that define a tunnel. The Mtp oligomers can be positioned between a first and second conductive liquid medium and the first or second conductive liquid medium can comprise the analyte.

Also provided are methods of inducing necrotic cell death in a subject. The methods comprise administering to the subject an isolated polypeptide comprising the carboxy-terminal domain of MtpA. The carboxy-terminal domain of MtpA can also be used in methods of treating or preventing excessive eye blinking, muscle pain disorders, hyperhidrosis, or cervical dystonia in a subject.

Further provided are methods of screening for an agent that modulates the activity of a Mtp porin. The methods comprise contacting a cell with the agent to be tested, wherein the cell comprises the Mtp, and determining the activity of the Mtp. An increase or decrease in the activity of the Mtp as compared to a control indicates that the agent modulates the activity of the Mtp.

Methods of screening for an agent that neutralizes a toxin produced by *Mycobacterium tuberculosis* are provided herein. The methods comprise contacting a cell with the agent to be tested, contacting the cell with the toxin, and detecting the level of cell death in the presence of the agent. A decrease in the level of cell death as compared to a control indicates the agent neutralizes the toxin.

The details of one or more embodiments are set forth in the accompanying drawings and the description below. Other features, objects, and advantages will be apparent from the description and drawings, and from the claims.

DESCRIPTION OF DRAWINGS

FIG. 1 shows a diagram of the construct encoding the Δbcg3960c (ΔMtpA) mutant of *M. bovis* BCG.

FIG. 2 shows the results of subcellular localization and outer membrane localization of MtpA (Rv3903c).

FIG. 3 shows that MtpA and its N-terminal domain are required for uptake of and growth on glycerol.

FIG. 7 shows the in vivo survival of the Δrv3903c (ΔmtpA) mutant.

FIG. 8 shows the nitric oxide resistance of *M. bovis* BCG. *M. bovis* BCG was treated with 100 mM sodium nitroferricyanide (III) dehydrate (SNP) in liquid Middlebrook 7H9 medium. Serial dilutions were spotted on Middlebrook 7H10 agar supplemented with 10% OADC. Plates were incubated at 37° C. for three weeks.

DETAILED DESCRIPTION

Figure 1A:
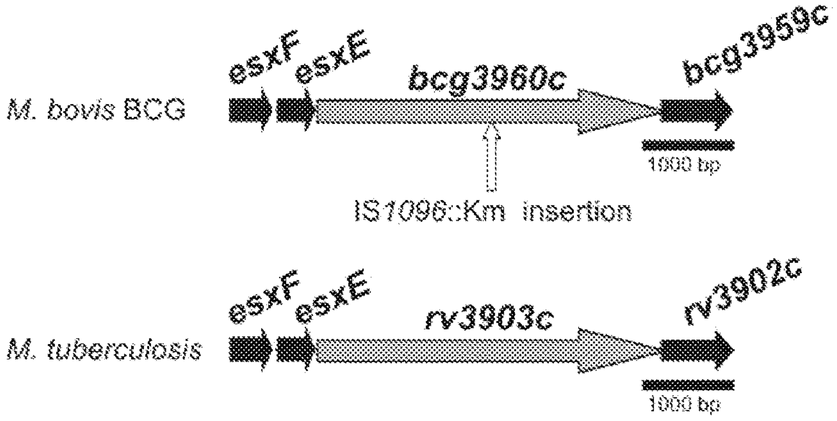
FIG. 1A shows the genomic region of the ML1012 mutant. The bcg3960c gene and its flanking genes are depicted. Black arrows represent open reading frames. The vertical arrow depicts the insertion of the transposon IS1096::Km. The sequence of the Bcg3960c protein is identical to that of Rv3903c of *M. tuberculosis*, furthermore, the flanking genes are identical in *M. bovis* BCG and Mtb as well.

Provided herein are isolated polypeptides comprising the amino-terminal domain of *Mycobacterium tuberculosis* porin A (MtpA). The polypeptide including the amino-terminal domain of MtpA can be a porin monomer. Optionally, the amino-terminal domain of MtpA comprises amino acids 1-443 of SEQ ID NO:1. Optionally, the isolated polypeptides comprise SEQ ID NO:1.

Also provided are isolated polypeptides comprising the carboxy-terminal domain of MtpA. The carboxy-terminal domain of MtpA can be a toxin. Optionally, the amino-terminal domain of MtpA comprises amino acids 650-846 of SEQ ID NO:1.

Optionally, in the polypeptides disclosed herein, the amino-terminal domain, the carboxy-terminal domain, or both the amino-terminal and carboxy-terminal domain of MtpA comprise one or more mutation(s).

Also provided are chimeric porin polypeptides. The chimeric porin polypeptides comprise a first polypeptide comprising the amino-terminal domain of a *Mycobacterium tuberculosis* porin (Mtp) and a second polypeptide comprising a selected antigen. The chimeric porin polypeptide comprises an antigen not naturally associated with the amino-terminal domain of Mtp. Optionally, the Mtp is MtpA. The amino-terminal domain of MtpA can, for example, comprise amino acids 1-443 of SEQ ID NO:1.

Optionally, the chimeric porin polypeptide can further comprise a third polypeptide comprising an amino acid linker. The amino acid linker can comprise a cleavage sequence.

The antigen can, for example, be selected from the group consisting of a viral antigen, a bacterial antigen, a fungal antigen, a prion antigen, and a parasitic antigen. An antigen is a molecule recognized by the immune system. A viral antigen can, for example, include any viral antigenic molecule or inactivated or attenuated virus (e.g., an envelope protein, a structural protein, and/or a capsid protein). Optionally, the viral antigen is envelope glycoprotein GP 120 of HIV. A bacterial antigen can, for example, include any bacterial antigenic molecule or inactivated or attenuated bacterium. Optionally, the bacterial antigen can be, for example, CFP-10 or ESAT-6 of *Mycobacterium tuberculosis*. A fungal antigen can, for example, include any fungal antigenic molecule or inactivated or attenuated fungus. Optionally, the fungal antigen is glucanase Crfl of *Aspergillus fumigatus*. A prion antigen can, for example, comprise any prion antigenic molecule or inactivated or attenuated prion. A parasitic antigen can, for example, include any parasitic antigenic molecule or inactivated or attenuated parasite. Optionally, the parasitic antigen is 19 kDa-merozoite surface protein-1 (MSP-1(19) of *Plasmodium falciparum*. As a general rule, surface antigens are most useful for provoking an immune response and can include cellular lipids proteins, proteoglycans or portions thereof.

Optionally, the antigen of interest comprises a cancer antigen. Cancer antigens can, for example, include any antigenic molecule associated with the cancer. An antigenic molecule associated with the cancer can, for example, include an antigenic portion of a polypeptide that is overexpressed in the cancer, an antigenic portion of a polypeptide that is expressed on the cell surface of cancer cells, or an antigenic portion of the proteoglycans or lipids on the cell surface of the cells of the cancer. Optionally, the cancer antigen is human prostate stem cell antigen (PSCA). Cancer antigens are known in the art, see, e.g., Sonpavde et al., Urol. Oncol. 25:451-9 (2007); Suri, Expert Opin. Biol. Ther. 6:379-89 (2006); Saleh et al., Curr. Pharm. Des. 11:3461-73 (2005), Bensalah et al., Prostate Cancer Prostatic Dis. 11:112-20 (2008); Disis et al., Breast Dis. 20:3-11 (2004); McNeel, Cancer Chemother. Biol. Response Modif. 22:247-61 (2005); Jager et al., Curr. Opin. Immunol. 14:178-82 (2002); Obata et al., Breast Cancer 6:305-11 (1999), which are incorporated herein for cancer antigens and methods of making and using them.

Also provided are *Mycobacterium tuberculosis* porin (Mtp) oligomers. The Mtp oligomers can, for example, comprise 2 to 12 of the disclosed isolated polypeptides comprising the amino-terminal domain of MtpA, the carboxy-terminal domain of MtpA, or both. For example, the isolated polypeptide comprises amino acids 1-443 of SEQ ID NO:1.

Also provided are nucleic acid sequences encoding the chimeric polypeptides or a single-chain *Mycobacterium tuberculosis* porin (Mtp) oligomer. The nucleic acid sequences encoding the single-chain Mtp oligomer comprise at least a first and a second porin encoding nucleotide sequence and a linker nucleic acid sequence encoding an amino acid linker. The first nucleotide sequence can, for example, encode a first Mtp monomer. The second nucleotide sequence can, for example, encode a second porin monomer, wherein the second encoded porin monomer is a *Mycobacterium* porin monomer. Optionally, the nucleic acid can further comprise a third, fourth, fifth, sixth, seventh, and eighth nucleotide sequence. The third, fourth, fifth, sixth, seventh, and eighth nucleotide sequences can, for example, encode a third, fourth, fifth, sixth, seventh, and eighth porin monomer, wherein the porin monomer is a *Mycobacterium* porin monomer.

Optionally, at least one of the encoded porin monomers comprises a wild-type *Mycobacterium tuberculosis* porin A (MtpA) monomer. Optionally, all of the encoded porin monomers of the single-chain oligomer comprise a wild-type MtpA monomer. The encoded wild-type MtpA monomer can comprise SEQ ID NO:1. Optionally, one or more of the encoded porin monomers can comprise amino acids 1-443 of SEQ ID NO:1.

The encoded amino acid linker can, for example, comprise 10 to 20 amino acids. Optionally, the encoded amino acid linker comprises 15 amino acids. Optionally, the encoded amino acid linker comprises a $(GGGGS)_3$ (SEQ ID NO:4) peptide sequence.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As discussed above, the polypeptides provided herein have a desired function. The polypeptide comprising the amino-terminal domain of MtpA functions as a porin monomer. The polypeptide comprising the carboxy-terminal domain of MtpA functions as a toxin. The chimeric porin polypeptide functions to elicit an immune response in a subject by providing an antigenic polypeptide to the subject.

As with all peptides, polypeptides, and proteins, including fragments thereof, it is understood that additional modifications in the amino acid sequence of amino-terminal or carboxy-terminal domains of MtpA or the chimeric porin polypeptide can occur that do not alter the function of the peptides, polypeptides, or proteins. Such modifications include conservative amino acid substitutions and are discussed in greater detail below. Thus, the polypeptides described herein can be modified so long as the desired function is maintained. It is understood that one way to define any known modifications and derivatives or those that might arise, of the disclosed genes and proteins herein, is through defining the modifications and derivatives in terms of identity to specific known sequences. Specifically disclosed are polypeptides which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the amino-terminal domain, carboxy-terminal domain, SEQ ID NO:1, or the chimeric porin polypeptide are provided herein. For example, provided are polypeptides which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to SEQ ID NO:1. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al. Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may be produced by human intervention (e.g., by mutagenesis of cloned DNA sequences), or may arise due to environmental influence (e.g., exposure to ultraviolet light), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |

TABLE 1-continued

Amino Acid Substitutions

| Amino Acid | Substitutions (others are known in the art) |
|---|---|
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods including the methods described in the Examples below. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, M13 primer mutagenesis and PCR mutagenesis.

Nucleic acids that encode the polypeptide sequences, variants, and fragments thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

Also provided are methods of treating or preventing a *Mycobacterium tuberculosis* (Mtb) infection in a subject with or at risk of developing a Mtb infection. A subject with Mtb includes subjects diagnosed with an Mtb infection. A subject at risk includes a subject with a known exposure or with a potential exposure to a Mtb source, include, for example, at a prison or medical facility. The methods comprise administering to the subject a first agent that modulates the activity of a *Mycobacterium tuberculosis* porin (Mtp) and a second agent that treats or prevents the Mtb infection. The Mtp can, for example, comprise *Mycobacterium tuberculosis* porin (MtpA).

The first agent can, for example, target the amino-terminal domain of MtpA. By targeting the amino-terminal domain of MtpA it is meant that the first agent can bind directly or indirectly to block the function of the amino-terminal domain. Optionally, the first agent targets amino acids 1-443 of SEQ ID NO:1. Optionally, the first agent modulates the activity of the Mtp by increasing the uptake of the second agent by the Mtp as compared to uptake in the absence of the first agent. Optionally, the first agent modulates the activity of the Mtp by decreasing the uptake of one or more nutrients or carbon sources by the Mtp as compared to the uptake in the absence of the agent.

Optionally, the one or more nutrients can be selected from the group consisting of carbon, oxygen, hydrogen, nitrogen, phosphorous, sulfur, potassium, magnesium, calcium, iron and trace elements. Optionally, the carbon source can be selected from the group consisting of sugars, amino acids, glycerol, fatty acids, lipids, and detergents. Nutrients and carbon sources for bacteria are known in the art, see, e.g., Lim, Microbiology, $3^{rd}$ Ed., Kendall/Hunt Publishing (2003).

The methods for treating or preventing a Mtb infection in a subject with or at risk of developing a Mtb infection can, for example, comprise administering to the subject a first agent that neutralizes a toxin produced by *Mycobacterium tuberculosis* and a second agent that treats or prevents the Mtb infection. By neutralizing a toxin, it is meant that the first agent eliminates or reduces the function of the toxin. Optionally, the toxin comprises the carboxy-terminal domain of *Mycobacterium tuberculosis* porin A (MtpA). The first agent can, for example, target a cleavage sequence of MtpA. The cleavage sequence of MtpA can be located between the amino-terminal domain and carboxy-terminal domain of MtpA. Optionally, the first agent blocks cleavage of the carboxy-terminal domain of MtpA from the amino-terminal domain of MtpA. By blocking cleavage, it is meant that the agent prevents cleavage of the MtpA polypeptide between the carboxy- and amino-terminal domains. Without intending to be limited by theory, the first agent can, for example, bind the cleavage sequence and prevent access to the cleavage sequence by the protease responsible for cleavage of the polypeptide. Alternatively, the first agent can target the protease responsible for cleavage and prevent that protease from cleaving the MtpA polypeptide.

The first agent can, for example, be selected from the group consisting of a nucleic acid molecule, a polypeptide, a small molecule, or a peptidomimetic. The nucleic acid molecule can, for example, be selected from the group consisting of an antisense sequence, a short inhibitory RNA (siRNA) sequence, or a microRNA (miRNA) sequence. The polypeptide can, for example, be an antibody or a fragment thereof.

The second agent can, for example, be selected from the group consisting of ampicillin, tetracycline, chloramphenicol, ethambutol, isoniazid, p-aminosalicylic acid, cycloserine, vancomycin, streptomycin, clarithomycin, erythromycin A, rifampicin, ciprofloxacin, ofloxacin, levofloxacin, moxifloxacin, and norfloxacin.

As used herein, a nucleic acid molecule can be a short-interfering RNA (siRNA) sequence or a micro-RNA (miRNA) sequence. A 21-25 nucleotide siRNA or miRNA sequence can, for example, be produced from an expression vector by transcription of a short-hairpin RNA (shRNA) sequence, a 60-80 nucleotide precursor sequence, which is subsequently processed by the cellular RNAi machinery to produce either a siRNA or miRNA sequence. Alternatively, a 21-25 nucleotide siRNA or miRNA sequence can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). A siRNA sequence preferably binds a unique sequence within the target mRNA with exact complementarity and results in the degradation of the target mRNA molecule. A siRNA sequence can bind anywhere within the target mRNA molecule. A miRNA sequence preferably binds a unique sequence within the target mRNA with exact or less than exact complementarity and results in the translational repression of the target mRNA molecule. A miRNA sequence can bind anywhere within the target mRNA sequence, but preferably binds within the 3' untranslated region of the target mRNA molecule. Methods of delivering siRNA or miRNA molecules are known in the art. See, e.g., Oh and Park, Adv. Drug. Deliv. Rev. 61(10):850-62 (2009); Gondi and Rao, J. Cell Physiol. 220(2):285-91 (2009); and Whitehead et al., Nat. Rev. Drug. Discov. 8(2):129-38 (2009).

As used herein, a nucleic acid molecule can be an antisense nucleic acid sequence. Antisense nucleic acid sequences can, for example, be transcribed from an expression vector to produce an RNA which is complementary to at least a unique portion of the target mRNA and/or the endogenous gene which encodes the target. Hybridization of an antisense nucleic acid under specific cellular conditions results in inhibition of target protein expression by inhibiting transcription and/or translation.

The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77, 1985) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

Also provided are methods of eliciting in a subject an immune response to an antigen. The methods comprise administering to the subject a modified *Mycobacterium*, wherein the modified *Mycobacterium* comprises any of the chimeric porin polypeptides disclosed herein. Optionally, the modified *Mycobacterium* comprises any of the chimeric porin polypeptides disclosed herein. Optionally, the modified *Mycobacterium* is selected from an attenuated *Mycobacterium tuberculosis* or *Mycobacterium Bovis* BCG. By attenuated, it is meant that the strain is modified to be less virulent than an unmodified strain. Strategies for using modified *Mycobacterium* are known in the art, see, e.g., Sambandamurthy and Jacobs, Microbes Infect. 7:955-61 (2005) and Zhang et al., Scand. J. Immunol. 72:349-57 (2010).

Also provided are methods of detecting an analyte in a conductive liquid medium. The method comprises applying an electric field to the *Mycobacterium tuberculsos* porin (Mtp) oligomers disclosed herein. The Mtp oligomers can, for example, have a vestibule and a constriction zone that define a tunnel, wherein the Mtp oligomer is positioned between a first conductive liquid medium and second conductive liquid medium. Optionally, the first or second conductive liquid medium comprises an analyte.

The method of detecting an analyte can, for example, comprise measuring an ion current as the analyte interacts with the tunnel to provide a current pattern. The appearance of a blockade in the current pattern indicates the presence of an analyte. Optionally, the methods comprise identifying the analyte, wherein identifying the analyte comprises comparing the current pattern to a known current pattern obtained using a known analyte under the same conditions.

The analyte can, for example, be selected from the group consisting of a nucleotide, a nucleic acid, an amino acid, a polypeptide, a protein, a polymer, a drug, an ion, a pollutant, a nanoscopic object, or a biological warfare agent. Optionally, the analyte is a polymer comprising more than one subunit. A polymer can, for example, comprise a polypeptide, a protein, or a nucleic acid.

The Mtp oligomers can, for example, be used to distinguish a first subunit of a polymer from at least a second subunit of the polymer. Distinguishing may comprise measuring the ion current produced as the first and second subunits separately translocate through the tunnel to produce a first and second current patter. The first and second current patters can, for example, differ from each other. Optionally, the Mtp oligomers can sequence the polymer. Sequencing the polymer can comprise measuring the ion current or optical signals as each unit of the polymer is separately translocated through the tunnel to provide a current pattern that is associated with each subunit of the polymer. Each current patter is compared to a known current patter of a known subunit under the same conditions, such that the polymer is sequenced.

The Mtp oligomers can, for example, also be used to determine the concentration, size, molecular weight, shape, or orientation of an analyte, or any combination thereof.

Also provided are methods of inducing necrotic cell death in a subject. Also provided are methods of treating or preventing excessive eye blinking, muscle pain disorders, hyperhidrosis, or cervical dystonia in a subject. The methods comprise administering to the subject an isolated polypeptide comprising the carboxy-terminal domain of MtpA. Optionally, the carboxy-terminal domain of MtpA comprises amino acids 650-834 of SEQ ID NO:1.

Also provided are methods of reducing wrinkles in a subject. The methods comprise administering into one or more muscles of the subject an isolated polypeptide comprising the carboxy-terminal domain of MtpA, wherein the contraction of the muscles is associated with wrinkles (e.g., facial muscles to reduce facial wrinkles). Optionally, the carboxy-terminal domain of MtpA comprises amino acids 650-834 of SEQ ID NO:1.

Further provided are methods of screening for an agent that modulates the activity of a Mtp. The methods comprise contacting a cell with the agent to be tested, wherein the cell comprises the Mtp, and determining the activity of the Mtp. An increase or decrease in the activity of the Mtp as compared to a control indicates that the agent modulates the activity of the Mtp. As used herein, a control can be a cell that is not contacted with the agent to be tested. Optionally, the Mtp is MtpA. Optionally, the Mtp comprises the amino-terminal domain of MtpA. The amino terminal domain of MtpA can, for example, comprise amino acids 1-443 of SEQ ID NO:1.

The activity of the Mtp can be selected from the group consisting of uptake of an antibiotic, output of antibiotic, and uptake of one or more nutrients or carbon sources. The antibiotic can be selected from the group consisting of ampicillin, tetracycline, chloramphenicol, ethambutol, isoniazid, p-aminosalicylic acid, cycloserine, vancomycin, streptomycin, clarithomycin, erythromycin A, rifampicin, ciprofloxacin, ofloxacin, levofloxacin, moxifloxacin, and norfloxacin. The carbon source can, for example, be glycerol.

Further provided are methods of screening for an agent that neutralizes a toxin produced by *Mycobacterium tuberculosis*. The methods comprise contacting the cell with the agent to be tested, contacting the cell with the toxin, and detecting the level of cell death in the presence of the agent. A decrease in cell death as compared to a control indicates the agent neutralizes the toxin. As used herein, a control can be a cell that is not contacted with the agent to be tested. Optionally, the toxin comprises the carboxy-terminal domain of MtpA. The carboxy-terminal domain of MtpA can, for example, comprise amino acids 650-834 of SEQ ID NO:1.

Provided herein are compositions containing the provided polypeptides, nucleic acid molecules, small molecules, and/or peptidomimetics and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in *Remington: The Science and Practice of Pharmacy,* $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the agent, e.g., the polypeptide, nucleic acid molecule, small molecule, and/or peptidomimetic, to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the nucleic acid molecule or polypeptide is administered by a vector comprising the nucleic acid molecule or a nucleic acid sequence encoding the polypeptide. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., *Retorviruses*, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infections viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter can be an inducible promoter (e.g. chemically or physically regulated promoter). A chemically regulated promoter can, for example, be regulated by the presence of alcohol, tetracycline, a steroid, or a metal. Optionally, the inducible promoter is an acetamide-inducible promoter. A physically regulated promoter can, for example, be regulated by environmental factors, such as temperature and light. The promoter can be a cell type specific promoter (e.g. neuronal-specific, renal-specific, cardio-specific, liver-specific, or muscle-specific). A cell-type specific promoter is only expressed in the cell-type in which it is intended to be expressed. The promoter can be a promoter that is expressed independent of cell type. Examples of promoters that can be expressed independent of cell type include the cytomegalovirus (CMV) promoter, the Raus sarcoma virus (RSV) promoter, the adenoviral E1A promoter, and the EF-1α promoter. Optionally, the promoter is a $ps_{myc}$ promoter.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The vectors also can include, for example, origins of replication, scaffold attachment regions (SARs), and/or markers. A marker gene can confer a selectable phenotype, e.g., antibiotic resistance, on a cell. This marker product is used to determine if the gene has been delivered to the cell and once delivered is being expressed. Examples of marker genes include the *E. coli* lacZ gene, which encodes β galactosidase, green fluorescent protein (GFP), and luciferase. Examples of suitable selectable markers for mammalian cells are dihydrofolate reductase (DHFR), thymidine kinase, neomycin, neomycin analog G418, hygromycin, blasticidin, and puromycin. When such selectable markers are successfully transferred into a mammalian host cell, the transformed mammalian host cell can survive if placed under selective pressure. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, Conn.) sequences typically are expressed as a fusion with the encoded polypeptide. Such tags can be inserted anywhere within the polypeptide, including at either the carboxy- or amino-terminus.

As used throughout, subject can be a vertebrate, more specifically a mammal (e.g., a human). The term does not denote a particular age or sex. Thus, adult and newborn subjects, whether male or female, are intended to be covered. As used herein, patient or subject may be used interchangeably and can refer to a subject with a disease or disorder (e.g., a *Mycobcaterium tuberculosis* (Mtb) infection or at risk for the same). The term patient or subject includes human and veterinary subjects.

A subject at risk of developing a disease or disorder (e.g., a Mtb infection) includes a subject with a known exposure or a potential exposure to *Mycobacterium tuberculosis* (e.g., due to employment at a prison or medical care facility) or due to the prevalence of *Mycobacterium tuberculosis* at a specific location (e.g., a prison or hospital), or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the agents described herein are administered to a subject prior to onset (e.g., before obvious signs of Mtb infection) or during early onset (e.g., upon initial signs and symptoms of Mtb infection). Prophylactic administration can occur for several days to years prior to the manifestation of symptoms of Mtb infection. Prophylactic administration can be used, for example, in the preventative treatment of subjects with a predisposition to Mtb infection (e.g., hospital workers). Therapeutic treatment involves administering to a subject a therapeutically effective amount of the agents described herein after diagnosis of an Mtb infection.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Methods

Chemicals and Enzymes.

Hygromycin B was purchased from Calbiochem (San Diego, Calif.). All other chemicals were purchased from Merck (Whitehouse Station, N.J.) or Sigma (St. Louis, Mo.) at the highest purity available. Enzymes for DNA restriction and modification were from New England Biolabs (Ipswich, Mass.) and Invitrogen (Carlsbad, Calif.). Oligonucleotides were obtained from IDT (Coralville, Iowa).

Bacterial Strains, Media and Growth Conditions.

*E. coli* DH5α was used for cloning experiments and was routinely grown in Luria-Bertani broth at 37° C. *M. smegmatis* strains were grown at 37° C. in Middlebrook 7H9 medium (Difco) supplemented with 0.2% glycerol and 0.01% Tyloxapol or on Middlebrook 7H10 plates supplemented with 0.5% glycerol. *M. bovis* BCG (Strain Institute Pasteur) was grown in Middlebrook 7H9 medium (Difco) supplemented with 0.2% glycerol, 0.01% Tyloxapol and 10% OADC (Remel; Lenexa, Kans.) or on Middlebrook 7H10 plates supplemented with 0.5% glycerol and 10% OADC (Remel). Antibiotics were used when required at the following concentrations: hygromycin (200 μg/ml for *E. coli,* 50 μg/ml for mycobacteria), kanamycin (30 μg/ml). Hartmans-de Bont (HdB) medium (Smeulders et al., J. Bacteriol. 181:270-83 (1999)) supplemented with 0.01% Tyloxapol and appropriated carbon source (1% Tween-80 or 0.1% glycerol) was used as a minimal medium for growth experiments.

Construction of Plasmids.

Plasmids used are listed in Table 2; oligonucleotides used are listed in Table 3. To construct a new integrative vector without a bla resistance cassette and with low copy number in *E. coli*, plasmid pML113 (Wolschendorf et al., J. Bacteriol. 189:2435-42 (2007)) was digested with SspI and ClaI followed by T4 Polymerase treatment to remove sticky ends. The pBR322 origin of replication was cloned in from pET21a(+) (Novagen; Madison, Wis.), digested with FspI and DraI. In order to be able to use PacI restriction site for further applications, the obtained plasmid was digested with PacI, followed by blunt-end reaction with T4 polymerase and re-ligation resulting in construction of pML2008. MspA expression cassette under control of $p_{imyc}$ was cloned from pMN013 (Stephan et al., Antimicrob. Agents Chemother. (2004)) by digestion with ClaI followed by fill-in reaction with T4 Polymerase and digestion with SpeI. The obtained fragment was cloned into pML2008 digested with SpeI and PmeI resulting in pML2009. PCR amplification of rv3903c (also referred to as *Mycobacterium tuberculosis* porin (MtpA)) was done from genomic DNA of H37Rv (obtained from Colorado State University as part of the National Institutes of Health (NIAID) Contract HHSN266200400091C entitled “Tuberculosis Vaccine Testing and Research Materials”) using the oligonucleotides CN1537 and CN1397, which introduced the PacI restriction site at the 5'-end and HindIII restriction site at the 3'-end. The obtained PCR fragment and pML2009 were digested with PacI and HindIII and ligated resulting in pML2010. To obtain complementation vector pML2046 for the N-terminal domain of MtpA (amino acids (aa) 1-444), PCR amplification was done using CN1537 and CN1729, followed by digestion with PacI and HindIII and ligation into pML2009 digested with the same enzymes. *M. smegmatis* expression vector pML2061 was obtained by digestion of pML2046 and pMN016 (Stephan et al., Mol. Microbiol. 58:714-30 (2005)) with PmeI and HindIII. To obtain a tagged version of MtpA, two step PCR amplification was employed: (1) the His-tag was added by using CN1393 (introduction of NdeI site on 5' end) and CN1824; (2) the HA-tag was added by using CN1393 and CN1825 (introduction of HindIII site on 3' end and EcoRV site between MtpA and tags). The obtained PCR fragment was digested with NdeI and HindIII and ligated into pNIT-1::gfp (Pandey et al., Tuberculosis 89:12-6 (2009)) digested with the same enzymes resulting in pML2024. To exchange the resistance cassette, pML2024 was digested with HpaI and XbaI and ligated into pMS2 (Kaps et al., Gene 278:115-24 (2001)) digested with EcoRV and XbaI to obtain pML2031. The nitrile-inducible vector pML2040 for the N-terminal domain of MtpA (aa 1-444) was obtained by PCR amplification of MtpA using CN1393 and CN1720 followed by NdeI and EcoRV digestion and ligation into pML2031 digested with the same enzymes. To construct the *E. coli* expression vector for the N-terminal domain of MtpA (aa 49-444), the gene was codon optimized for efficient expression in *E. coli* and synthesized by GenScript (Piscataway, N.J.). Domain 1 (without signal sequence), was amplified by PCR using two step protocol: (i) 5'-end Strep-tag was introduced with CN1806 and 3'-end HA-tag was introduced with CN1809, (ii) 5'-end NdeI site was introduced with CN1753 and 3'-end His-tag and HindIII was introduced with CN1781. The obtained PCR fragment was digested with NdeI and HindIII and cloned into pET-28b(+) digested with the same enzymes.

TABLE 2

| Plasmids | |
|---|---|
| Plasmid | Relevant Genotype and Properties |
| pET-21(+) | T7 promoter, transcription start and terminator, His-tag, lacI, bla, pBR322 ORI, 5443 bp |
| pET-28b(+) | T7 promoter, transcription start and terminator, His-tag, lacI, aph, pBR322 ORI, 5368 bp |
| pMN013 | ColE1 origin, hyg, oriM, $p_{imyc}$-mspA, 6000 bp |
| pMN016 | ColE1 origin, hyg, oriM, $p_{smyc}$-mspA, 6164 bp |
| pML113 | FRT-hyg-FRT, bla, attP, ColE1 origin, 4365 bp |
| pNIT-1::gfp | ColE1 origin, aph, oriM, $p_{nit1}$-egfp, $p_{nit2}$-nitR, 6912 bp |
| pML970 | ColE1 origin, hyg, oriM, $p_{imyc}$-phoA-HA, 6895 bp |
| pMV6015.1 | ColE1 origin, hyg, oriM, $p_{hsp60}$-PE_PGRS33-HA, 6895 bp |
| pML2008 | pPR322 origin, attP, FRT-hyg-int-FRT, 5749 bp |

TABLE 2-continued

| Plasmids | |
|---|---|
| Plasmid | Relevant Genotype and Properties |
| pML2009 | pPR322 origin, attP, FRT-hyg-int-$p_{imyc}$-mspA-FRT, 6676 bp |
| pML2010 | pPR322 origin, attP, FRT-hyg-int-$p_{imyc}$-rv3903c-FRT, 8557 bp |
| pML2024 | ColE1 origin, aph, oriM, $p_{nit1}$-rv3903c-HA-His, $p_{nit2}$-nitR, 8789 bp |
| pML2031 | ColE1 origin, aph, oriM, $p_{nit1}$-rv3903c-HA-His, $p_{nit2}$-nitR, 9078 bp |
| pML2040 | ColE1 origin, aph, oriM, $p_{nit1}$-domain 1 of rv3903c-HA-His, $p_{nit2}$-nitR, 7884 bp |
| pML2046 | pPR322 origin, attP, FRT-hyg-int-$p_{imyc}$-domain1 of rv3903c-FRT, 7360 bp |
| pML2061 | ColE1 origin, hyg, oriM, $p_{imyc}$-domain 1 of rv3903c, 6684 bp |
| pML2069 | T7 promoter, transcription start and terminator, Strep-tagII-codon adapted domain 1 of rv3903c-HA-His, lacI, aph, pBR322 ORI, 6532 bp |

TABLE 3

| Oligonucleotides | |
|---|---|
| Oligo. | Sequence (5' to 3') |
| CN1393 | CGCATATGGCGCCGTTGGCGGTCGATCCCGC (SEQ ID NO: 5) |
| CN1394 | CGAAGCTTCTACTGTCGCAACACCCCGCGC (SEQ ID NO: 6) |
| CN1537 | GCTTAATTAACAGAAAGGAGGATTTCAACTATCATGGCGCCGTTGGCGGTCGATCCCGC (SEQ ID NO: 7) |
| CN1720 | CGGATATCCGGTGTCGTCGGCTCAAGC (SEQ ID NO: 8) |
| CN1729 | GCTTGAGCCGACGACACCGAAGCTTCG (SEQ ID NO: 9) |
| CN1753 | CGCATATGTGGAGCCACCCGCAGTTCGAAAAA (SEQ ID NO: 10) |
| CN1781 | CGAAGCTTTA**GTGGTGGTGGTGGTGGTG**AGTACTGGCGTAGTCCGGCAC (SEQ ID NO: 11) |
| CN1806 | GCCACCCGCAGTTCGAAAAAGCAGGTGCAGTGTTTGGC (SEQ ID NO: 12) |
| CN1809 | *GGCGTAGTCCGGCACGTCGTA*CGGGTACGGCGTGGTCGGTTCCAG (SEQ ID NO: 13) |
| CN1824 | AGTACT*GGCGTAGTCCGGCACGTCGTACGGGTA*GATATCCTGTCGCAACACCCCGCGC (SEQ ID NO: 14) |
| CN1825 | TAAAGCTTTA**GTGGTGGTGGTGGTGGTG**AGTACTGGCGTAGTCCGGCAC (SEQ ID NO: 15) |

Restriction sites are underlined.
The sequence shown in italics is the sequence of the HA tag.
The sequence shown in bold is the sequence of the His tag.

Subcellular Fractionation of *M. Smegmatis.*

Experiments were carried out as described previously with some modifications (Song et al., Tuberculosis 88:526-44 (2008)). Briefly, *M. smegmatis* $mc^2155$ containing nitrile-inducible full-length MtpA (pML2024) or the N-terminal domain (pML2040) were grown until an $OD_{600}$ of 0.2 was reached. 5 μM isovalernitrile was added to induce protein expression. After 48 hours of growth, cultures were harvested by centrifugation and washed twice with PBS (140 mM NaCl, 2 mM KCl, 10 mM $K_2HPO_4/KH_2PO_4$ pH 7.4) containing 1 mM PMSF and 1 mM EDTA. The cells were resuspended and lysed by sonication (10 minutes, 12 Watt output power). Unbroken cells were removed by low speed centrifugation (4,000×g for 15 minutes). The resulting supernatant was ultra-centrifuged at 100,000×g for 1 hour to separate cytosolic proteins (SN-100.1) from membrane fraction (P-100.1). P-100.1 was washed extensively to remove all cytosolic and membrane-attached proteins. All samples were mixed with protein loading buffer (160 mM Tris-Cl pH 7.0, 12% SDS, 32% glycerol, 0.4% Bromophenol blue), boiled for 10 minutes and loaded on the 10% SDS-PAGE gel. The protein gel was blotted overnight at 50 mA in transfer buffer (25 mM Tris base, 192 mM Glycine, 0.1% SDS, 20% methanol) onto a polyvinylidene difluoride (PVDF) membrane (Amersham; Piscataway, N.J.). Tagged versions of full-length Rv3903c and the N-terminal domain were detected with anti-HA-HRP antibody (Sigma), MspA was detected with rabbit antiserum against MspA (pAK #813) (Kartmann et al., J. Bacteriol. 181:6543-6 (1999)) using ECL plus kit (Pierce; Rockford, Ill.). LabWorks (UVP; Upland, Calif.) chemoluminescence imaging system and the software were used to visualize and quantify the luminescence.

Proteinase Accessibility Assay.

The assays were done as described previously (Song et al., Tuberculosis 88:526-44 (2008)). PE-PGRS-$33_{HA}$ (pMV61015.1) (Cascioferro et al., Mol. Microbiol. 66:1536-47 (2007)) and $PhoA_{HA}$ (pML970) (Song et al., Tuberculosis 88:526-44 (2008)) were used as controls for proteinase accessibility assay. Strains were grown as described above. Proteinase K treatment was done at 4° C. for 30 minutes.

Purification of the N-Terminal Domain of MtpA.

Nitrile induction of the N-terminal domain of MtpA (aa 1-444) was done in *M. smegmatis* $mc^2155$ carrying plasmid pML2040 as described above. The cells were harvested, washed twice with PBS buffer, and disrupted at 4° C. using a Sonicator 3000 ultrasonic liquid processor (Misonix, Inc.; Farmingdale, N.Y.) (15 minutes, 12 W output power). The pellet was obtained by low speed centrifugation at 4,000×g and was treated with 1 mg/ml of lysozyme and 0.01 mg/ml of DNaseI for 2 hours at 37° C. The sonication step was performed again as described above. The pellet obtained by low speed centrifugation (4,000×g) contains the majority of the N-terminal domain of MtpA and therefore was used for further purification steps. The proteins were solubilized by incubation with 0.8% sodium dodecyl sulphate (SDS) overnight at 37° C. Non-soluble material was removed by centrifugation at 16,000×g for 10 minutes at room temperature. Extracted proteins were then loaded onto a 1.7 ml POROS 20MC Ni-NTA column (BioLogic duoflow, BioRad HPLC system) (Bio-Rad; Hercules, Calif.) and eluted off using an imidazole gradient from 0 M to 0.5 M. Purification was done according to the manufacturer's protocol. Anion-exchange purification was done next using 1.7 ml POROS 20 HZ anion-exchange column as described elsewhere (Siroy et al., J. Biol. Chem. 283:17827-37 (2008)). Elution was done using salt concentration gradient ranging from 10 mM to 2 M NaCl. To perform gel purification, protein samples were incubated at 37° C. for 1 hour and loaded on 8% SDS-PAGE gel. To visualize proteins, reverse staining by imidazole-zinc salts was performed (Fernandez-Patron et al., Biotechniques 12; 564-73 (1992)) and subsequently confirmed using Western blot analysis. Protein bands of interest were excised from the gel, and eluted using D-Tubes (Novagen). Electroelution was done using cathode buffer (0.1 M Tris-HCl pH 8.25, 0.1 M Tricine, 0.1% SDS) overnight at 50 mA (4° C.). The obtained protein was dialyzed overnight at 4° C. using D-Tube Dialyzer kit (EMD Chemicals; Gibbstown, N.J.) (according to manufacturer's protocol) against PBS containing 0.5% n-octylpolyethylene oxide (OPOE, Alexis Biochemicals; Farmingdale, N.Y.). The channel forming activity of the purified protein was analyzed using the lipid bilayer method. Protein concentrations were determined using BCA kit (Pierce). In addition, a calibration curve with known amounts of bovine serum albumin (BSA) was used to estimate protein concentrations in Coomassie Blue-stained SDS-PAGE gels using the imagine analysis software (LabWorks 4.6, UVP). For protein expression and purification of the N-terminal domain of MtpA (aa 49-444) from *E. coli*, BL21 carrying pML2069 plasmid was used. Using a previously published protocol (Song et al., Tuberculosis 88:526-44 (2008)), the N-terminal domain was found to be localized both in soluble fractions and in inclusion bodies. Soluble fractions were pooled together and Ni-affinity purification was performed as described above. Strep-tag batch purification was done using Strep-Tactin Sepharose (IBA; Gottingen, Germany) according to the manufacturer' instruction. 0.5% OPOE was added to the elution buffer. Gel elution, dialyzes and protein concentration determination were done as described above.

Channel Activity Analysis.

The single-channel conductance of the N-terminal domain of MtpA was analyzed as described previously (Siroy et al., J. Biol. Chem. 283:17827-37 (2008)). As a negative control for contaminations or intrinsic ability of buffer to form channels in bilayer, a gel peace of approximately the same size which does not contain any detectable proteins was cut from the SDS-PAGE gel and treated the same way as described above for the N-terminal domain of MtpA. At least 3 different membranes were recorded (at 10 and 100 mV) using this sample before addition of the protein.

Glycerol Uptake Experiments.

Glycerol uptake experiments were carried out as described previously (Danilchanka et al., Antimicrob. Agents Chemother. 52:3127-34 (2008b)) with some modifications. The cells were harvested at an $OD_{600}$ of 0.5-1.0 by centrifugation, washed twice in the uptake buffer (50 mM Tris pH 6.9, 15 mM KCl, 10 mM $(NH_4)_2SO_4$, 1 mM $MgSO_4$, 0.02% Tyloxapol), and resuspended in the same buffer (mean dry weight is 0.5-1 mg/ml). The cells were pre-incubated at 37° C. for 5 minutes (*M. smegmatis*) or 15 minutes (*M. bovis* BCG) before addition of [$^{14}C$] glycerol (specific activity: 146 mCi/mmol). The final concentration of radioactively-labeled glycerol was 1.5 μM for *M. smegmatis* and 3 μM for *M. bovis* BCG. The experiment was performed in triplicate at least two independent times.

Determination of Antibiotic Resistance.

Determination of the minimal inhibitory concentration (MIC) was done using the microplate Alamar Blue assay (MABA) (Franzblau et al., J. Clin. Microbiol. 36:362-6 (1998)) with some modifications (Danilchanka et al., Antimicrob. Agents Chemother. 52:2503-11 (2008); Danilchanka et al., Antimicrob. Agents Chemother. 52:3127-34 (2008b)). The final drug concentrations were as follows: for isoniazid and ethambutol, 0.03125-1 μg/ml; for streptomycin and rifampicin, 0.04 to 1.28 μg/ml; for levofloxacin, ofloxacin and clarithromycin, 0.0625-2 μg/ml; for p-aminosalicylic acid and moxifloxacin, 0.25-8 μg/ml; for ciprofloxacin and norfloxacin, 0.5-16 μg/ml; for chloramphenicol and cycloserine, 1 to 32 μg/ml; for vancomycin, 2.5 to 80 μg/ml; for erythromycin A and tetracycline, 8 to 256 μg/ml; for ampicillin, 30 to 960 μg/ml. The MABA was performed in triplicate at least two independent times.

Sensitivity to Nitric Oxide.

*M. bovis* BCG strains were grown in 7H9/OADC/0.01% Tyloxapol to an $OD_{600}$ of 2. The cultures were pelleted down, washed and re-suspended in 1/10 of original volume. 0.1-ml aliquots of the suspension were added to 0.9 ml of fresh media containing 0 mM, 5 mM, 25 mM and 100 mM sodium nitroferricyanide (III) dehydrate (SNP, Sigma). Each suspension was incubated at 37° C. (200 rpm) for 0, 1, 3 or 7 days. Serial dilutions of the cultures were plated on 7H10/OADC/Hyg plates and incubated at 37° C. for 3 weeks, after which colony forming units (CFU) were counted. The data were recalculated as the percent survival ([number of CFU exposed at day X/number of CFU unexposed at day X]×100%). Each strain was tested in triplicate; assay was repeated three independent times.

Macrophage Experiments.

Human acute monocytotic leukemia cells (THP-1) were maintained as described previously (Jordao et al., Cell Microbiol. 10:529-48 (2008)). Differentiation of THP-1 monocytes into macrophages was done overnight with 50 mM phorbol 12-myreistate 13-acetate (PMA). Human monocyte-derived macrophages (HMDM) were obtained from a buffy coat preparation kindly provided by Instituto Português do Sangue, and prepared as previously described (Jordao et al., Cell Microbiol. 10:529-48 (2008)). The THP-1 cells were infected with a multiplicity of infection (MOI) of 20 and HMDMs were infected with MOI between 1 and 3. In each experiment, after 3 hours of infection, the cells were washed 3 times with PBS to remove non-internalized bacteria. At different time points after infection (3 hours, 1, 3, 5 and 7 days), the cells were washed with PBS and lysed with 1% Igepal (Sigma) solution in water. Serial dilutions were performed in water and plated on Middlebrook 7H10 medium supplemented with 10% OADC. Colony forming units (CFU) were counted upon 2 weeks of incubation at 37° C. When required, HMDM were treated with human IFN-γ (200 IU) overnight before infection.

Analysis of Secondary Structure of Rv3903c.

Analysis was done as described previously (Siroy et al., J. Biol. Chem. 283:17827-37 (2008)).

Statistical Analysis.

Data were presented as mean±standard deviation; p values were calculated using Student t test, and a P value of <0.05 was considered to be significant.

Example 1: Characterization of the Δrv3903c (ΔMtpA) Mutant

In a previous attempt to identify outer membrane proteins of Mtb involved in the uptake of small hydrophilic compounds, a transposon library of *M. bovis* BCG was constructed and screened for mutants resistant to ampicillin (Danilchanka et al., Antimicrob. Agents Chemother. 52:2503-11 (2008)). There were no potential outer membrane proteins in this library identified based on criteria previously established for prediction of mycobacterial outer membrane proteins (Song et al., Tuberculosis 88:526-44 (2008)). However, OmpATb is an outer membrane protein of Mtb which does not have a classical Sec-signal sequence (Alahari et al., J. Bacteriol. 189:6351-8 (2007)) as observed for porins of gram-negative bacteria (de Keyzer et al., Cell Mol. Life. Sci. 60:2034-52 (2003)). Therefore, the ampicillin-resistant mutants in the library were re-analyzed for hypothetical proteins that have the properties of known porins with the exception of a signal sequence (Song et al., Tuberculosis 88:526-44 (2008)). One of the mutants in the screen, ML1012, contains an insertion in bcg3960c that encodes for a hypothetical alanine-proline-rich protein (FIG. 1A). Bcg3960c of *M. bovis* BCG is identical to Rv3903c of Mtb, therefore, for simplicity reasons the bcg3960c *M. bovis* BCG transposon mutant is referred to as the Δrv3903c mutant or the ΔMtpA mutant. Inactivation of MtpA results in 32-fold increased resistance of *M. bovis* BCG to ampicillin (Table 4), (Danilchanka et al., Antimicrob. Agents Chemother. 52:2503-11 (2008)). Although the protein does not have a classical Sec-signal sequence (SignalP probability<0.1) (Bendtsen et al., J. Mol. Biol. 340:783-95 (2004)), further analysis indicated that MtpA has an "extended" signal sequence found in some proteins of the Type V secretion system (Jacob-Dubuisson et al., Mol. Micriobiol. 40:306-13 (2001); Szabady et al., Proc. Natl. Acad. Sci. USA 102:221-6 (2005)). The predicted signal sequence of MtpA consists of an N-terminal extension (amino acids (aa) 1-20), followed by canonical domains associated with the Sec-signal sequence: charged domain (aa 21-24), hydrophobic domain (aa 25-36) and cleavage domain (aa 37-45).

TABLE 4

Antibiotic resistance of the ΔMtpA mutant.

| Antibiotic | MIC for *M. Bovis* BCG (μg/ml) Wild-type | ΔMtpA | ΔMtpA + MspA | ΔMtpA + MtpA | Resistance factor |
|---|---|---|---|---|---|
| Class A | | | | | |
| Ampicillin | 30 | 960 | 60 | 60 | 32 |
| Tetracycline | 31.25 | >250 | 62.5 | 62.5 | >8 |
| Chloramphenicol | 4 | 64 | 8 | 8 | 16 |
| Ethambutol | 0.125 | >1 | 0.125 | 0.125 | >8 |
| Isoniazid | 0.25 | >1 | 0.25 | Nd | >4 |
| p-aminosalicylic acid | 2 | >8 | 2 | 2 | >4 |
| cycloserine | 4 | 8 | 4 | 4 | 2 |
| Class B | | | | | |
| Vancomycin | 5 | 20 | 10 | 10 | 4 |
| Streptomycin | 0.16 | 0.64 | 0.32 | 0.32 | 4 |
| Clarithromycin | 0.125 | >2 | 0.5 | 0.25 | >16 |
| Class C | | | | | |
| Erythromycin A | 16 | >256 | 32 | 16 | >16 |
| Rifampicin | 0.008 | >0.128 | 0.032 | 0.032 | 16 |
| Class D | | | | | |
| Ciprofloxacin | 1 | 2 | 2 | 2 | 2 |
| Ofloxacin | 0.25 | 0.5 | 0.25 | 0.25 | 2 |
| Levofloxacin | 0.125 | 0.5 | 0.125 | 0.125 | 4 |
| Moxifloxacin | 0.5 | 1 | 0.5 | 0.5 | 2 |
| Norfloxacin | 1 | 4 | 2 | 2 | 4 |

Antibiotics were grouped into four classes: A. small and hydrophilic antibiotics (MW from 102 to 481 g/mol); B. large (MW from 484 to 1450 g/mol) and hydrophilic; C. large (MW from 612 to 823 g/mol) and hydrophobic; D. fluroquinolones (MW from 319 to 402 g/mol). The minimal inhibitory concentrations (MIC) are listed. The resistance factor R is given by the ratio $MIC_{\Delta MtpA}/MIC_{wt}$.

Figure 1B:
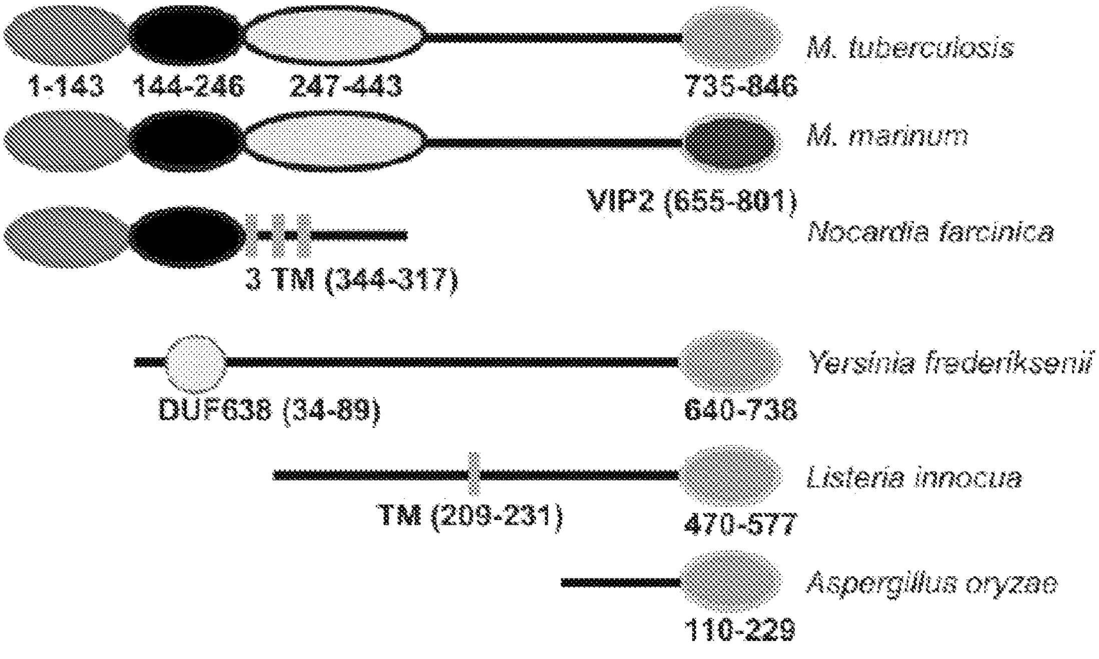
FIG. 1B shows a diagram based on BLAST analysis of Rv3903c domains of various bacterial species. VIP2, ADP-ribosylating toxin family; TM: transmembrane helices; DUF638, possible hemagglutinin.

Of note, extended signal sequences with a remarkably conserved N-terminal extended signal peptide region have only been found in Gram-negative bacterial proteins from the classes β- and γ-Proteobacteria, and exclusively in proteins secreted via the Type V secretion pathway, such as autotransporters, two-partner secretion system, and trimeric autotransporters (Desvaux et al., FEMS Microbiol. Lett. 264:22-30 (2006)). However, proteins of the Type V secretion system have not been characterized in mycobacteria yet. Based on available sequence information, only genomes of slow-growing mycobacteria such as Mtb, *M. bovis* and *M. bovis* BCG have full-length homologues of the MtpA protein. BLAST analysis (FIG. 1B) in combination with bioinformatic predictions (Table 5), suggest that MtpA is organized into three domains: an N-terminal domain (aa 1-443) specific for mycolic-acid containing bacteria, an unstructured domain 2 (aa 444-734) and a C-terminal domain high in β-sheet content (735-846) (FIG. 1B). The N-terminal domain contains several conserved regions: region A (aa 1-105) is a full protein in several actinobacteria, region B (aa 140-230) is conserved in *nocardia* and mycobacteria and region C (aa 230-444) is found exclusively in mycobacteria. While the function of C-terminal domain was unknown, homologues found in some bacteria and ascomycota are predicted to be hemagglutinin-like secreted proteins or adhesin/hemolysis-like proteins.

TABLE 5

| Structure and analysis of MtpA (Rv3903c) | | | | |
|---|---|---|---|---|
| Description | % β-strand | Amphiphilicity | Cysteines | pI |
| MtpA (Rv3903c) | 0.09 | 0.49 | 6 | 5.3 |
| Domain 1 (1-443) | 0.1 | 0.46 | 5 | 4.7 |
| Domain 2 (444-734) | 0.03 | 0.25 | 0 | 5.8 |
| Domain 3 (735-864) | 0.23 | 0.53 | 1 | 6.1 |

The number of β-strands with a length of five or more amino acids was predicted by using the Jnet algorithm (http://www.compbio.dundee.ac.uk/jpred). Amphiphilicity is defined as the faction of alternating hydrophilic and hydrophobic residues in β-strands.

Example 2: MtpA is an Outer Membrane Protein

Figure 2A:
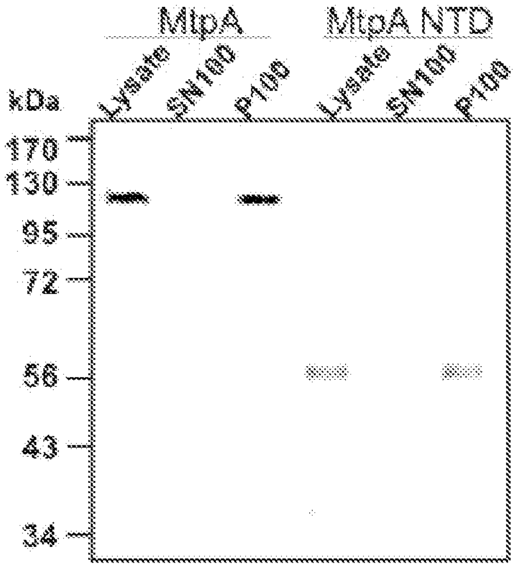
FIG. 2A shows the cell wall fractionation assay. Subcellular fractions of *M. smegmatis* $mc^2155$ encoding either nitrile-inducible full-length $MtpA_{HA\text{-}His}$ (pML2024) or the N-terminal domain $(1\text{-}444\ aa)_{HA\text{-}His}$ (pML2040) (domain 1) were analyzed. Cells were lysed by sonication (Lysate), and the membrane fraction P100 was separated from fraction SN100 containing soluble cytosolic and periplasmic proteins by ultracentrifugation. Proteins were detected using a mouse anti-HA-HRP conjugate. EZ-Run™ pre-stained Rec protein ladder was used to estimate sizes of proteins.
Figure 2B:
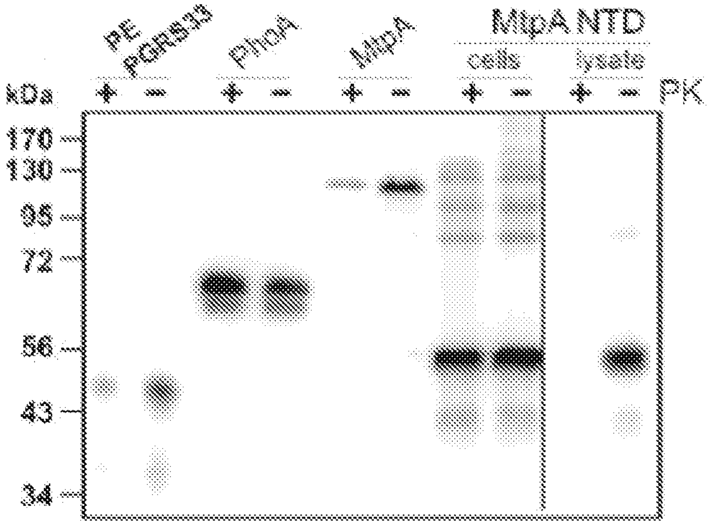
FIG. 2B shows the results of the surface accessibility experiments using proteinase K. *M. smegmatis* $mc^2155$ carrying the plasmid pML970 ($p_{smyc}$-$phoA_{HA}$) or pMV6015.1 ($p_{hsp60}$-$PE\_PGRS33_{HA}$) were used as assay controls. Strains were incubated with (+) or without (−) proteinase K at 4° C. for 30 minutes. Proteinase K was added to whole cells or lysed cell lysates. Extracts of whole cells and cell lysates were separated on an SDS-PAGE (10%) gel. Experiments were carried out at least two independent times.

To examine whether MtpA is a surface associated protein, the full-length protein and its N-terminal domain (aa 1-444) (domain 1) tagged with HA and His-tags at the C-termini, under control of a nitrile-inducible promoter was cloned and expressed them in *M. smegmatis* $mc^2155$. Both proteins were tested to determine if they were localized with membranes using subcellular fractionation. The cell envelope fraction (P100) and the fraction containing water-soluble cytoplasmic and periplasmic proteins (SN100) were separated by ultracentrifugation of whole cell lysates (100,000× g) (Song et al., Tuberculosis 88:526-44 (2008)). Both the N-terminal domain and the full-length MtpA were associated with the membrane fraction P100 and not with the soluble fraction SN100 (FIG. 2A). Similar fractionation profiles have been found previously for other known mycobacterial outer membrane proteins such as MspA, OmpATb, and Rv1698 (Song et al., Tuberculosis 88:526-44 (2008)). Because the P100 fraction contains inner and outer membrane proteins and membrane-associated proteins, the surface accessibility of MtpA was determined. To this end, accessibility of MtpA to proteinase K was tested (Song et al., Tuberculosis 88:526-44 (2008)), which is based on the inability of proteinase K to penetrate the mycobacterial cell envelope. Therefore, only proteins with extracellular loops are digested in whole cells. As controls for the assay, the surface protein $PE\_PGRS33_{HA}$ was overexpressed (Cascioferro et al., Mol. Microbiol. 66:1536-47 (2007)), which was significantly digested in the presence of proteinase K, and a periplasmic protein $PhoA_{HA}$ (Siroy et al., J. Biol. Chem. 283:17827-37 (2008)), which was unaffected by the proteinase K treatment (FIG. 2B). Similarly to $PE\_PGRS33_{HA}$, full-length MtpA was largely degraded when treated with the proteinase K, demonstrating that MtpA is surface accessible. The combination of the membrane association and surface accessibility experiments indicates that MtpA is an outer-membrane protein. By contrast, the N-terminal domain of MtpA (domain 1) was not degraded by proteinase K in whole cells but was fully degraded when cell lysates were treated with the proteinase K (FIG. 2B). Based on the membrane association of the N-terminal domain of MtpA, it suggests that the protein is targeted to the outer membrane; however, it lacks extracellular loops which are accessible to the proteinase K degradation in the whole cells.

Example 3: MtpA is Required for Uptake of Glycerol in *M. Bovis* BCG

Figure 3A:
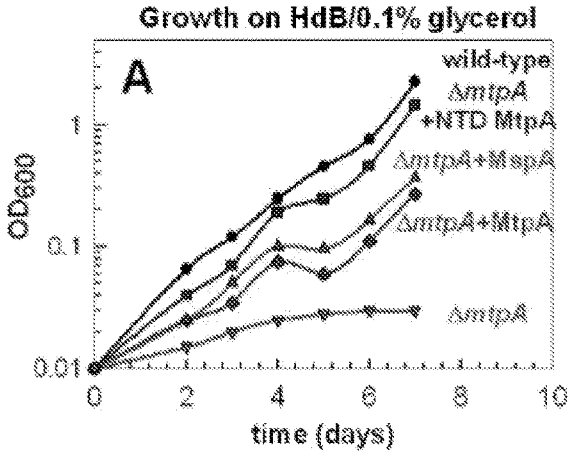
FIG. 3A shows a graph demonstrating the growth of the *M. bovis* BCG mtpA mutant on minimal HdB medium containing 0.1% glycerol as a sole carbon source.
Figure 3B:
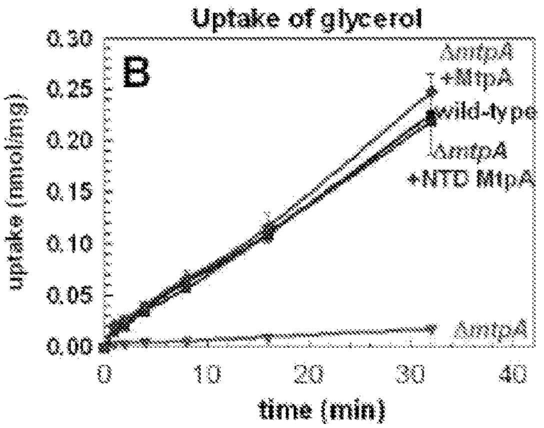
FIG. 3B shows a graph demonstrating accumulation of $^{14}C$-labelled glycerol by *M. bovis* BCG ΔmtpA mutant and complemented strains.

Mutations in porins of gram-negative bacteria and *M. smegmatis* can result in decreased growth rates due to decreased uptake of small or hydrophilic solutes such as glucose and glycerol when used as sole carbon sources (Liu and Ferenci, J. Bacteriol. 180:3917-22 (1998); Stephan et al., Mol. Microbiol. 58:714-30 (2005)). To determine if uptake of nutrients in slow-growing mycobacteria is dependent on MtpA, the growth of wild-type *M. bovis* BCG was analyzed in comparison to the ΔMtpA mutant. No difference in growth was observed when oleic acid was used as a sole carbon source, suggesting that the utilization of hydrophobic solutes as nutrients in the ΔMtpA mutant is the same as in the wild-type strain of *M. bovis* BCG and the ΔMtpA mutant does not have an intrinsic growth defect. Using rich Middlebrook 7H9 medium containing glycerol, glucose and oleic acid as carbon sources, a slight growth defect was observed for the ΔMtpA mutant. To identify the compound utilization of which was impaired in this medium in the ΔMtpA mutant, minimal Hartmans-de Bond (HdB) media was used with various carbon sources. Growth of the ΔMtpA mutant was only minimal when 0.1% glycerol was added as the sole carbon source (FIG. 3A). Next, it was examined whether the observed growth delay of the ΔMtpA mutant is due to the lack of glycerol transport. Uptake experiments revealed that $[^{14}C]$ glycerol accumulation in the ΔMtpA mutant was drastically reduced compared to that of the wild-type strain suggesting that MtpA plays major role in the uptake of glycerol in *M. bovis* BCG (FIG. 3B).

The bioinformatic analysis (FIG. 1B) indicates that MtpA is composed of several domains. To examine this hypothesis, the full-length protein or the N-terminal domain were cloned into identical integrative vectors and the growth of the resulting strains was examined in liquid medium. Partial complementation of the ΔMtpA mutant growth defect was observed by both the N-terminal domain (aa 1-444) and the full-length length MtpA in 7H9 Middlebrook medium. While full-length MtpA only partially complemented the growth defect of the mutant in liquid minimal medium with glycerol as the sole carbon source, the N-terminal domain (domain 1) of MtpA fully complemented the growth defect of the MtpA mutant (FIG. 3A). Furthermore, an increase in the growth rate of the ΔMtpA mutant in both rich and minimal liquid medium was also observed upon expression of mspA, a gene encoding general porin of *M. smegmatis* (FIG. 3A). These results indicate that the MtpA mutant is deficient in the uptake of glycerol due to the lack of transport through the outer membrane of *M. bovis* BCG. Furthermore, expression of the N-terminal domain (aa 1-444) of MtpA is sufficient for the growth and uptake complementation of the MtpA mutant of *M. bovis* BCG.

Example 4: The N-Terminal Domain of MtpA has Channel Activity

Figure 4A:
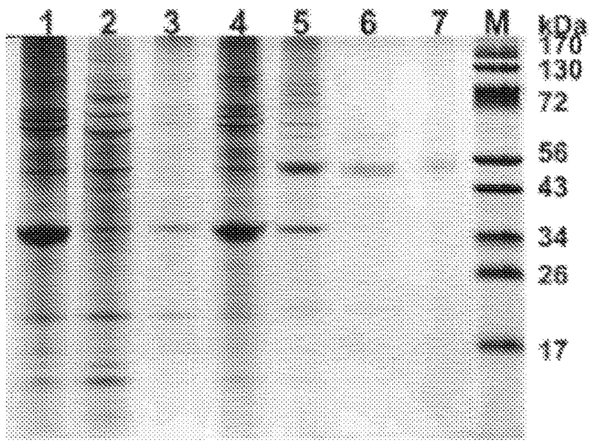
FIG. 4 shows purification and single channel recordings of the N-terminal domain of Rv3903c (MtpA) purified from *M. smegmatis*. Expression of the N-terminal domain of rv3903c$_{HA\text{-}His}$ in *M. smegmatis* and purification by chromatography. The N-terminal domain of Rv3903c (aa 1-444) was expressed in *M. smegmatis* mc$^2$155 using the nitrile-inducible plasmid pML2040. Samples were separated on a 10% polyacrylamide gel and stained with Coomassie blue (FIG. 4A) or detected in a Western blot using anti-HA antibody (FIG. 4B). Lanes M, molecular mass marker; pellet 1 (lane 1) and soluble fraction 1 (lane 2) after sonication; pellet 2 (lane 3) and soluble fractions 2 (lane 4) after overnight extraction with 0.8% SDS at 37° C.; lane 5, $Ni^{2+}$-affinity purification; lane 6, anion-exchange purification; lane 7, SDS-PAGE gel purification.
FIG. 4C shows a tracking of single channel recording of purified Rv3903c (aa 1-444) in lipid bilayer experiments. The current (I) of a diphytanoylphosphatidylcholine (DPhPC) membrane bathing in 1 M KCl was recorded after the addition of less than 100 ng of purified protein to both sides of the membrane (final concentration, <10 ng/ml). Frequency of opening (FIG. 4D) and closing (FIG. 4E) events was derived from single channel conductance of 14 membranes. The main single channel conductance is 4.0±0.2 nS.
Figure 4B:
Figure 4C:
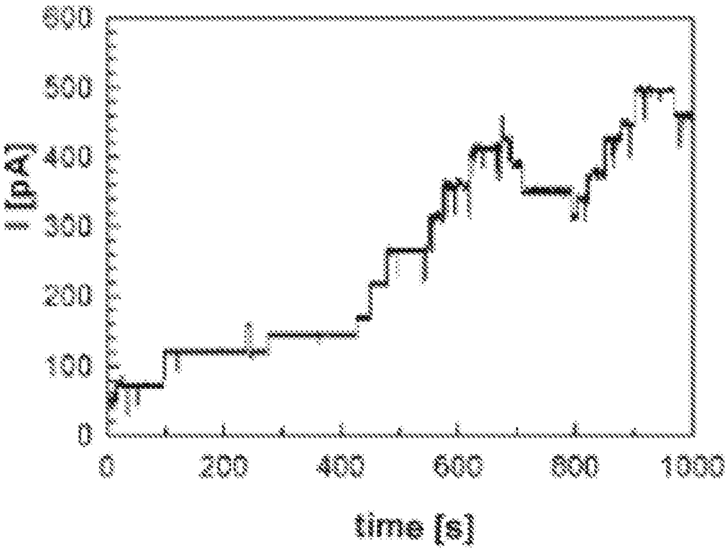
Figure 4D:
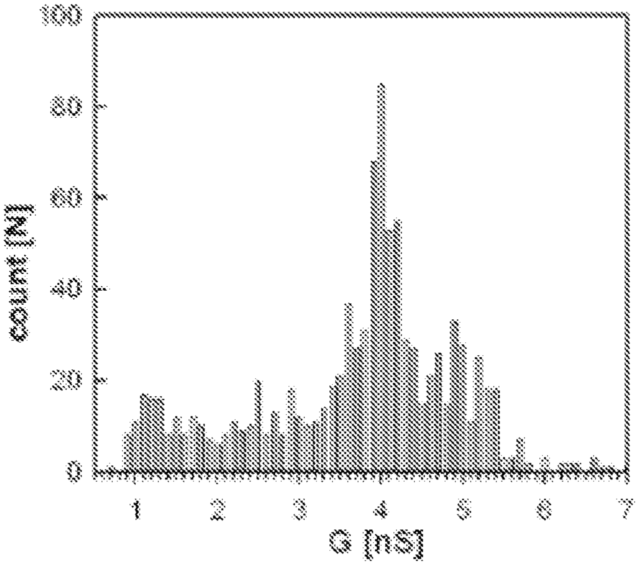
Figure 4E:
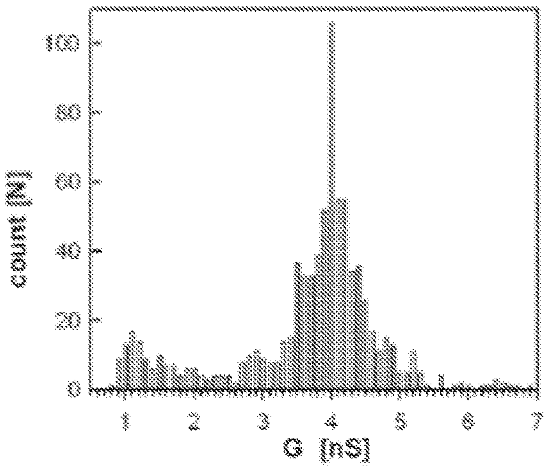

Based on the observation that both the N-terminal domain of MtpA and MspA complements the growth defect of the ΔMtpA mutant, this domain was speculated to have porin activity. Porins are water-filled channel proteins that enable diffusion of small molecules and ions that are not able to diffuse through lipid membranes directly (Schulz, Curr. Opin. Struct. Biol. 6:485-90 (1996)). Passage of ions through porins can be measured electrophysiologically using a planar lipid bilayer assay. This method detects the incorporation of channel proteins into planar lipid membranes, which corresponds in discrete increases in the membrane current measured over time (Benz et al., Biochim. Biophys. Acta 511:305-19 (1978)). To this end, the N-terminal domain (aa 1-444) of MtpA was expressed under the control of a nitrile-inducible promoter in *M. smegmatis*. The N-terminal domain of MtpA was extracted from the pellet fraction with 0.8% SDS at 37° C. and purified on $Ni^+$-NTA affinity column followed by anion-exchange purification. To exclude the possibility that the measured channel activity originates from other protein contaminants not detected using Coomassie staining, the protein band corresponding to the N-terminal domain of MtpA was excised from SDS-PAGE gel and purified using electroelution (FIGS. 4A and 4B). No insertion events were detected when the storage buffer containing detergent was added to the lipid bilayer, demonstrating that the buffer/detergent alone does not have an intrinsic ability to form channels and does not contain any contaminating proteins with channel activity. Addition of less than 100 ng of purified N-terminal domain of MtpA to the same membrane resulted in a stepwise increase in the current (FIG. 4C). More than 100 pores from several different protein preparations were recorded. The most frequent single channel conductance was 4.0±0.2 nS (FIGS. 4D and 4E).

Figure 5A:
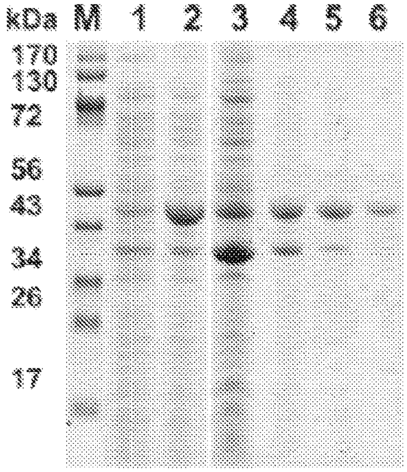
FIG. 5 shows purification and single channel recordings of the N-terminal domain of Rv3903c (MtpA) purified from *E. coli*. The N-terminal domain of Rv3903c (aa 49-444) was expressed in *E. coli* BL21 using plasmid pML2069. The samples were separated on a 10% polyacrylamide gel stained with Coomassie blue (FIG. 5A). Lane M, molecular mass marker; soluble fractions of BL21/pML2069 before (lane 1) and after (lane 2) induction with isopropyl-β-D-thiogalactopyranoside; lane 3, whole cell lysate after sonication; lane 4, $Ni^{2+}$-affinity purification; lane 5, strep-tag purification; lane 7, SDS-PAGE gel purification.
FIG. 5B shows a tracking of single channel recording of purified Rv3903c (aa 49-444) in lipid bilayer experiments. The current (I) of a DPhPC membrane bathing in 1 M KCl was recorded after the addition of less than 100 ng of purified protein to both sides of the membrane.
Figure 5B:
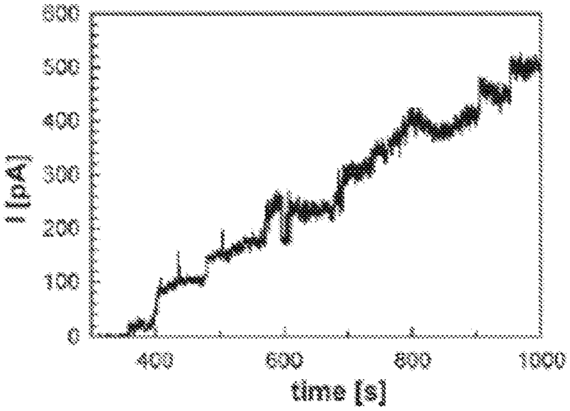

To eliminate the possibility that the observed channel activity of the N-terminal domain of MtpA results from a co-purified contaminant protein of *M. smegmatis*, expression of the protein was carried out in *E. coli*. A truncated N-terminal domain of MtpA (aa 49-444) was codon optimized and cloned into T7-expression vector, containing an N-terminal Strep-tag, and C-terminal HA- and His-tags. The N-terminal domain of MtpA was purified by $Ni^{2+}$- and Strep-tag affinity chromatography and gel elution (FIG. 5A). Reconstitution of purified N-terminal domain of MtpA into planar lipid bilayers resulted in stepwise increases in conductance (FIG. 5B). As these steps were not observed in control experiments, when only buffer containing detergent was added to the bilayer, it can be concluded that the observed channel activity is caused by the presence of the N-terminal domain of MtpA (aa 49-444). Moreover, the single channel conductance of the N-terminal domain of MtpA purified from *M. smegmatis* (FIGS. 4D and 4E) and *E. coli* (FIG. 5B) was almost identical indicating that the N-terminal domain of MtpA has porin activity.

Figure 6:
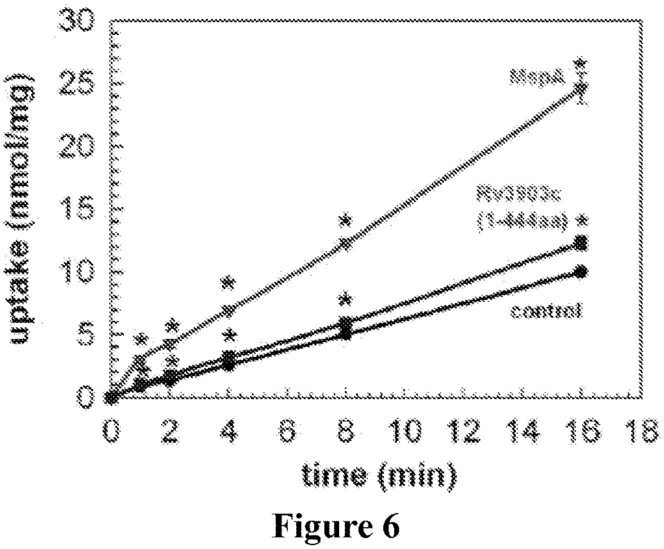
FIG. 6 shows glycerol uptake by a control *M. smegmatis* ML16 strain (ΔmspA ΔmspB ΔmspC, circles), a ML16+pMN016 strain ($P_{smyc}$-MspA, inverted triangles), or a ML16+pML2061 strain ($p_{imyc}$-Rv3903c (aa 1-444), squares). The assay was performed at 37° C. at a final concentration of 3 μM of [$^{14}C$] glycerol. The uptake rate is expressed as nmol of glycerol per milligram of cells. The uptake experiment was done in triplicate and is shown with standard deviations.

Previously, it has been shown that the uptake of small hydrophilic molecules in *M. smegmatis* is mediated by Msp-like porins (Stahl et al., Mol. Microbiol. 40:451-64 (2001); Stephan et al., Mol. Microbiol. 58:714-30 (2005)). Furthermore, a reduction in the number of porins results in a decreased growth rate (Stephan et al., Mol. Microbiol. 58:714-30 (2005)). Therefore, if the N-terminal domain of MtpA has a porin function, an increase in the rate of growth and nutrient uptake would be observed in a *M. smegmatis* porin mutant upon expression of the N-terminal domain of MtpA. When an untagged N-terminal domain of MtpA (aa 1-444) was expressed in ML16, a triple porin mutant of *M. smegmatis* (ΔmspA ΔmspB ΔmspD) (Stephan et al., Mol. Microbiol. 58:714-30 (2005)), a statistically significant increase in an accumulation of [$^{14}$C] glycerol was observed for this strain compared to ML16 (FIG. 6). However, the level of [$^{14}$C] glycerol accumulation upon expression of the N-terminal domain of MtpA was much lower compared to the control ΔmspA ΔmspB ΔmspD strain that was expressing mspA. These data suggest that the N-terminal domain of MtpA has outer membrane transport activity, albeit less than that of MspA. It is based on the porin activity of Rv3903c that the name of MtpA (for *Mycobacterium tuberculosis* porin A) is suggested.

Example 5: MtpA is Required for Uptake of Nutrients In Vivo

Figure 7A:
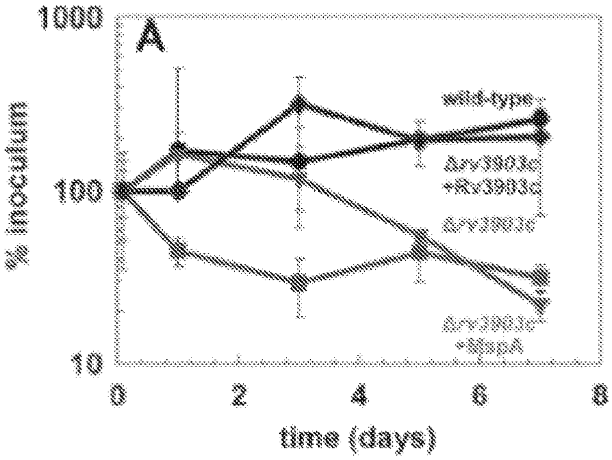
FIG. 7A shows a graph demonstrating the survival of *M. bovis* BCG in the THP-1 cell line. THP-1 cells were infected with wild-type *M. bovis* BCG (ML383, circles), the Δrv3903c mutant (ML386, triangles), and the Δrv3903c mutant complemented with either MspA (ML387, squares) or Rv3903c (ML388, diamonds) with an MOI of 20. Three hours after infection, macrophages were washed with PBS to remove non-internalized bacteria. Serial dilutions of lysed macrophages were plated at indicated time points after infection and colony forming units (CFUs) were enumerated after 2 weeks of incubation. CFUs were normalized according to the original inoculums of each strain.

Deletion of porins in *M. smegmatis* results in improved survival in macrophages due to reduced uptake of bactericidal components present in the phagosome (Fabrino et al., Microbes Infect. 11:868-75 (2009); Purdy et al., Mol. Microbiol. 73:844-57 (2009)). To define the role of MtpA for survival of Mtb in macrophages, human acute monocytic leukemia cells (THP-1) were infected with wild-type *M. bovis* BCG, the ΔMtpA mutant, or the mutant complemented with either full-length MtpA or mspA. As reported previously, THP-1 cells retained a constant low level of live wild-type *M. bovis* BCG bacteria over seven days of infection (FIG. 7A) (Jordao et al., Cell Microbiol. 10:529-48 (2008)). By contrast, the ΔMtpA mutant was rapidly killed after the first 3 days of infection. Upon complementation with MtpA, the observed phenotype was fully reversed demonstrating that MtpA is required for the uptake of nutrients and survival of *M. bovis* BCG in macrophages. Expression of MspA in the ΔMtpA mutant drastically decreased survival of the strain especially during initial stages of infection (FIG. 7A) suggesting that the functions of MspA and MtpA in macrophages are substantially different.

Example 6: MtpA Mediates Resistance to Nitric Oxide In Vitro and In Vivo

Figure 8A:
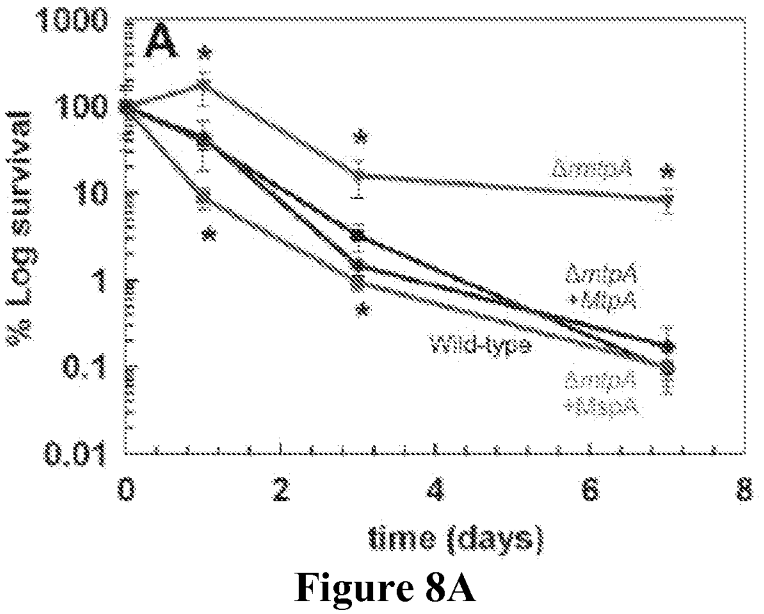
FIG. 8A shows a graph demonstrating the survival of wild-type *M. bovis* BCG (circles), the ΔmtpA mutant (inverted triangles), and the ΔmtpA mutant complemented with MspA (squares) or MtpA (diamonds). CFUs were normalized to the original inoculum. Experiments were done in triplicate and repeated three independent times. * $p<0.05$ for the wild-type strain vs. the ΔmtpA mutant or the wild-type strain vs. the ΔmtpA+MspA strain were determined using a Student t-test.
Figure 8B:
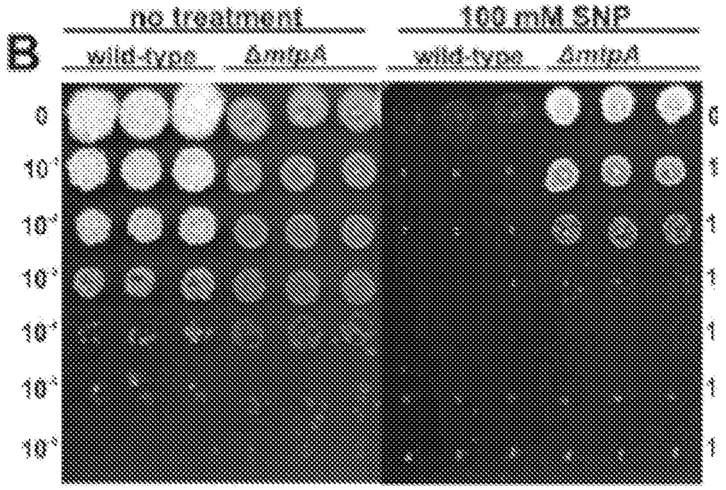
FIG. 8B shows a growth assay demonstrating the survival of wild-type *M. bovis* BCG and the ΔmtpA mutant after 7 days of treatment with 100 mM SNP.

The production of reactive nitrogen and oxygen intermediates plays a role in control of tuberculosis infection (MacMicking et al., Annu. Rev. Immunol. 15:323-50 (1997)). Previously it has been shown that the absence of msp porin genes confers resistance of *M. smegmatis* to nitric oxide (Fabrino et al., Microbes Infect. 11:868-75 (2009)). To investigate if MtpA is important for the resistance of slow-growing mycobacteria to nitric oxide, wild-type *M. bovis* BCG, the ΔMtpA mutant, or the mutant complemented with either full-length MtpA or mspA were treated with the nitric oxide donor sodium nitroferricyanide (III) dehydrate (SNP). Treatment of all strains with SNP in liquid Middlebrook 7H9 medium reduced the number of colonies recovered in a dose- and time-dependent manner (FIGS. 8A and 8B). The number of bacteria recovered for the wild-type strain was at least 100-fold reduced compared to the ΔMtpA strain (FIG. 8B). Expression of MtpA in the ΔMtpA strain fully restored the nitric oxide sensitivity of *M. bovis* BCG suggesting that *M. bovis* BCG is highly resistant to nitric oxide in the absence of MtpA (FIG. 8A). Overexpression of mspA in the ΔMtpA mutant resulted in almost complete clearance of the strain after 24 hours of treatment (FIG. 8A), thus confirming the previous observations that MspA-mediated uptake of toxic compounds leads to a decrease in survival under nitric oxide stress.

Figure 7B:
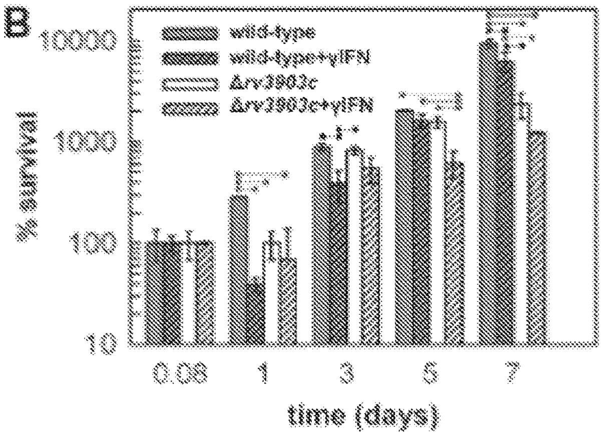
FIG. 7B shows a graph demonstrating the role of nitric oxide in survival of wild-type and the Δrv3903c mutant of *M. bovis* BCG. Human monocyte-derived macrophages (HMDMs) were infected with wild-type *M. bovis* BCG (grey) or the Δrv3903c mutant (white) with an MOI between 1 and 3. When required, HMDMs were treated with human IFN-γ (200 IU) overnight before infection (striped bars).

To determine if increased resistance of the ΔMtpA strain to nitric oxide has any advantages in vivo, infection of human monocyte-derived macrophages (HMDM) with wild-type *M. bovis* BCG was done with or without γ-interferon treatment. γ-Interferon is known to induce nitric oxide synthase activity in macrophages with a significant increase in nitric oxide levels after the first two days of infection with *M. bovis* BCG (Jordao et al., Cell Microbiol. 10:529-48 (2008)). Consistent with that, both wild-type and the ΔMtpA strains grew steadily over the course of infection in untreated HMDM, however, less bacteria were recovered for the mutant compared to the wild-type strain. This was especially pronounced on day 7 of infection (FIG. 7B). A drastic decrease in bacteria recovered was observed during the first 2 days of infection of γ-interferon stimulated HMDMs for the wild-type strain. Interestingly, no significant difference was observed in the survival of the ΔMtpA mutant when macrophages were treated with γ-interferon compared to untreated cells suggesting that absence of MtpA protects cells from the detrimental effects of nitric oxide in vivo.

Example 7: Absence of MtpA Confers a Multidrug Resistant Phenotype in *M. Bovis* BCG Lack of porins in gram-negative bacteria confers only low level resistance to small, hydrophilic drugs (Nikaido, Microbiol. Mol. Biol. Rev. 67:593-656 (2003)), while loss of porins in *M. smegmatis* result in higher resistance levels (Danilchanka et al., Antimicrob. Agents Chemother. 52:3127-34 (2008)). Uptake pathways for drugs in slow-growing mycobacteria have not been identified thus far. However, it has been suggested that porins mediate uptake of β-lactam antibiotics, ethambutol, isoniazid and streptomycin (Stephan et al., Antimicrob. Agents Chemother. 48:4163-70 (2004)). To determine if drug resistance of Mtb is mediated by MtpA, a microplate Alamar Blue assay (MABA) was employed. The resistance of *M. bovis* BCG to several small, hydrophilic antibiotics (Table 4, group A) was increased drastically in the absence of MtpA. For example, a 32- and 16-fold increased minimal inhibitory concentration (MIC) was observed for ampicillin and chloramphenicol respectively in the ΔMtpA strain while the resistance to the anti-tuberculosis drugs ethambutol, isoniazid and p-aminosalicylic acid (PAS) was increased more than eight-fold. Surprisingly, MICs for large and hydrophobic antibiotics such as erythromycin and rifamicin were also significantly increased in the ΔMtpA mutant (Table 4, group C). The resistance of the ΔMtpA strain expressing MspA or MtpA to small or/and hydrophilic antibiotics was identical to that of the wild-type *M. bovis* BCG (Table 4, groups A, D) suggesting that MtpA makes *M. bovis* BCG more susceptible to these drugs and that MspA and MtpA function by a similar mechanism.

Example 8: The C-Terminal Domain (CTD) of MtpA has Toxin Activity

Figure 9A:
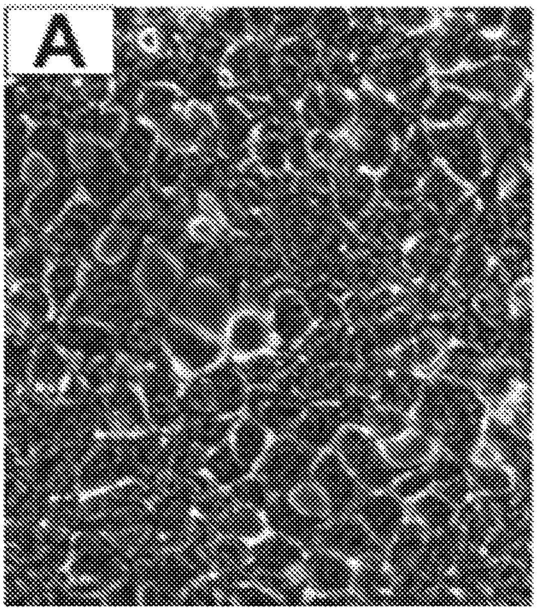
FIGS. 9A-C show micrographs demonstrating the survival of human 293T cells upon expression of empty vector (FIG. 9A), wild-type carboxy-terminal domain of MtpA (FIG. 9B), and a mutant carboxy-terminal domain of MtpA (CTDM1) (FIG. 9C).
Figure 9B:
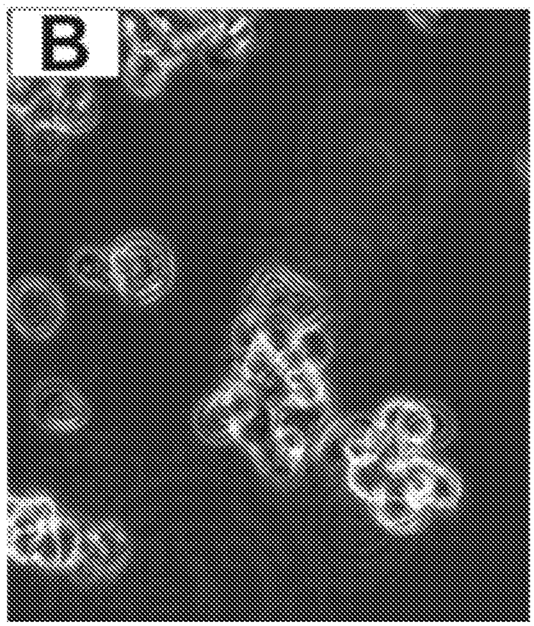
Figure 9C:
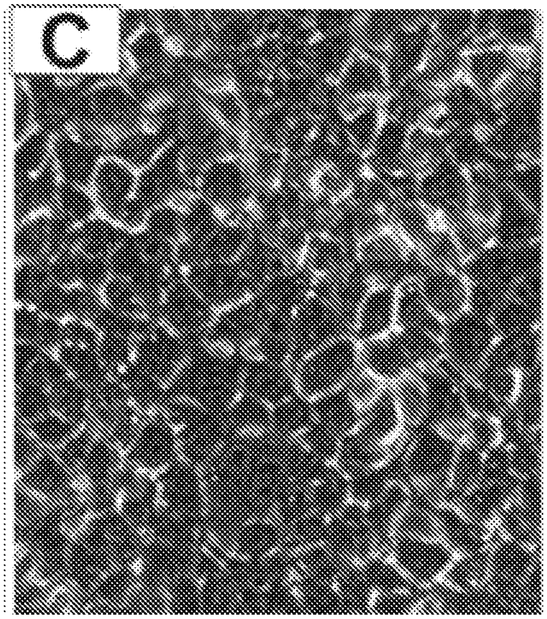

Attempts to express the MtpA CTD in vivo failed in *M. smegmatis, E. coli*, and *Saccharomyces cerevisiae* while in vitro (cell-free) expression allowed recovery of minute amounts of protein. To test whether the CTD of MtpA is toxic in mammalian cells, a pRK7-based vector (Graycar et al., Mol. Endocrinol. 3:1977-86 (1989)) containing the MtpA CTD fused with an HA-tag under control of the cytomegalovirus (CMV) promoter was transiently transfected into the human 293T cell line. Microscopy of cells 24 hours after transfection revealed that the majority of cells were dead (FIG. 9B) compared to cells transfected with a gfp-containing vector (FIG. 9A). To show that cell death was associated with activity of the CTD and not due to overexpression, a screen for non-toxic mutants of the CTD was performed. As expression of the CTD in *E. coli* is toxic, it was hypothesized that CTD-Gfp translational fusions will be fluorescent only in clones that contain point mutations or in-frame deletions of the CTD. As expected, no fluorescent clones with the wt sequence of the CTD were obtained. However, four different mutants (CTDM1-4) containing point mutations were identified based on Gfp-fluorescence: CTDM1 (G818E), CTDM2 (A811E), CTDM3 (G752V) and CTDM4 (G662D/R788L). The mutant CTDM1 was completely non-toxic in human 293T cells (FIG. 9C). These results show that MtpA contains a previously uncharacterized bacterial toxin domain, highlighting the assumption that mycobacterial OM proteins function by novel mechanisms.

Figure 9D:
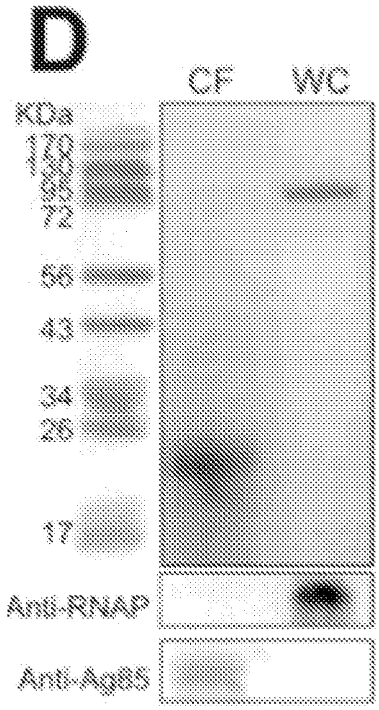
FIG. 9D shows a Western blot demonstrating that the MtpA carboxy-terminal domain is cleaved upon expression of MtpA. MtpA was detected in culture filtrate (CF) and whole cells (WC) using anti-HA antibodies. To show the efficient separation of CF and WC fractions, anti-RNA polymerase antibody (RNAP) and an antibody against the secreted protein Ag85 were used.

Activity of many bacterial toxins requires secretion (Type I and III) or cleavage on the cell surface (Type V). To examine which of these mechanisms applies to MtpA, whole cells and culture filtrates of *M. bovis* BCG and Mtb ΔmtpA strains containing MtpA C-terminally tagged with HA and His-tags were analyzed. Using anti-HA antibodies, full-length MtpA was detected in whole cells, and a ~24 kDa cleaved protein was detected in the concentrated culture filtrate (FIG. 9D), indicating that the CTD is shuttled to the OM as a full-length protein and is subsequently cleaved and released into the CF. Furthermore, the cleavage site of the CTD was identified by mass-spectrometry. The organization of MtpA with an OM channel domain and a toxin domain resembles the organization of autotransporters (Type Va secretion) such as VacA of *Helicobacter pylori* (Cover & Blanke, Nat. Rev. Microbiol. 3:320-32 (2005)), although the domains are organized differently compared to Gram-negative bacteria. As the similarity of autotransporters is limited to their OM channel domains, it is not surprising that mycobacterial autotransporters have not been found to date as the structure of the mycobacterial OM is vastly different from that of Gram-negative bacteria.

```
MtpA (Rv3903c)
                                          SEQ ID NO: 1
MAPLAVDPAALDSAGGAVVAAGAGLGAVISSLTAALAGCAGMAGDDPAGA

VFGRSYDGSAAALVQAMSVARNGLCNLGDGVRMSAHNYSLAEAMSDVAGR

AAPLPAPPPSGCVGVGAPPSAVGGGGGAPKGWGWVAPYIGMIWPNGDSTK

LRAAAVAWRSAGTQFALTEIQSTAGPMGVIRAQQLPEAGLIESAFADAYA

STTAVVGQCHQLAAQLDAYAARIDAVHAAVLDLLARICDPLTGIKEVWEF

LTDQDEDEIQRIAHDIAVVVDQFSGEVDALAAEITAVVSHAEAVITAMAD

HAGKQWDRFLHSNPVGVVIDGTGQQLKGFGEEAFGMAKDSWDLGPLRASI

DPFGWYRSWEEMLTGMAPLAGLGGENAPGVVESWKQFGKSLIHWDEWTTN

PNEALGKTVFDAATLALPGGPLSKLGSKGRDILAGVRGLKERLEPTTPHL

EPPATPPRPGPQPPRIEPPESGHPAPAPAAKPAPVPANGPLPHSPTESKP

PPVDRPAEPVAPSSASAGQPRVSAATTPGTHVPHGLPQPGEHVPAQAPPA

TTLLGGPPVESAPATAHQPQWATTPAAPAAAPHSTPGGVHSTESGPHGRS

LSAHGSEPTHDGASHGSGHGSGSEPPGLHAPHREQQLAMHSNEPAGEGWH

RLSDEAVDPQYGEPLSRHWDFTDNPADRSRINPVVAQLMEDPNAPFGRDP

QGQPYTQERYQERFNSVGPWGQQYSNFPPNNGAVPGTRIAYTNLEKFLSD

YGPQLDRIGGDQGKYLAIMEHGRPASWEQRALHVTSLRDPYHAYTIDWLP

EGWFIEVSEVAPGCGQPGGSIQVRIFDHQNEMRKVEELIRRGVLRQ

Amino-terminal domain of MtpA (Rv3903c)
                                          SEQ ID NO: 2
MAPLAVDPAALDSAGGAVVAAGAGLGAVISSLTAALAGCAGMAGDDPAGA

VFGRSYDGSAAALVQAMSVARNGLCNLGDGVRMSAHNYSLAEAMSDVAGR

AAPLPAPPPSGCVGVGAPPSAVGGGGGAPKGWGWVAPYIGMIWPNGDSTK

LRAAAVAWRSAGTQFALTEIQSTAGPMGVIRAQQLPEAGLIESAFADAYA

STTAVVGQCHQLAAQLDAYAARIDAVHAAVLDLLARICDPLTGIKEVWEF

LTDQDEDEIQRIAHDIAVVVDQFSGEVDALAAEITAVVSHAEAVITAMAD

HAGKQWDRFLHSNPVGVVIDGTGQQLKGFGEEAFGMAKDSWDLGPLRASI
```

-continued

DPFGWYRSWEEMLTGMAPLAGLGGENAPGVVESWKQFGKSLIHWDEWTTN

PNEALGKTVFDAATLALPGGPLSKLGSKGRDILAGVRGLKERL

Carboxy-terminal domain of MtpA (Rv3903c)

SEQ ID NO: 3

RLSDEAVDPQYGEPLSRHWDFTDNPADRSRINPVVAQLMEDPNAPFGRDP

-continued

QGQPYTQERYQERFNSVGPWGQQYSNFPPNNGAVPGTRIAYTNLEKFLSD

YGPQLDRIGGDQGKYLAIMEHGRPASWEQRALHVTSLRDPYHAYTIDWLP

EGWFIEVSEVAPGCGQPGGSIQVRIFDHQNEMRKVEELIRRGVLRQ

What is claimed is:

1. A chimeric porin polypeptide comprising a first polypeptide comprising a fragment of a *Mycobacterium tuberculosis* porin and a second polypeptide comprising an antigen, wherein the fragment comprises an amino-terminal domain of the *Mycobacterium tuberculosis* porin comprising amino acids 1-443 of SEQ ID NO:1 or an amino terminal domain of the *Mycobacterium tuberculosis* porin comprising an amino acid sequence that has at least 90% identity to amino acids 1-443 of SEQ ID NO:1, wherein the fragment is not the full-length *Mycobacterium tuberculosis* porin.

2. The chimeric porin polypeptide of claim 1, wherein the fragment comprises an amino-terminal domain of the *Mycobacterium tuberculosis* porin consisting of amino acids 1-443 of SEQ ID NO:1.

3. A method of eliciting in a subject an immune response to an antigen, the method comprising administering to the subject a modified *Mycobacterium*, wherein the modified *Mycobacterium* comprises the chimeric porin polypeptide of claim 2.

4. The chimeric polypeptide of claim 1, wherein the antigen is a viral antigen, a bacterial antigen, a fungal antigen, a prion antigen, a parasitic antigen or a cancer antigen.

5. The chimeric polypeptide of claim 2, wherein the antigen is a viral antigen, a bacterial antigen, a fungal antigen, a prion antigen, a parasitic antigen or a cancer antigen.

* * * * *